(12) United States Patent
McArthur et al.

(10) Patent No.: US 7,534,891 B2
(45) Date of Patent: May 19, 2009

(54) QUINOLINE DERIVATIVES AS H3R INVERSE AGONISTS

(75) Inventors: Silvia Gatti McArthur, Basel (CH); Cornelia Hertel, Muenchenstein (CH); Matthias Heinrich Nettekoven, Grenzach-Wyhlen (DE); Susanne Raab, Basel (CH); Hans Richter, Grenzach-Wyhlen (DE); Olivier Roche, Folgensbourg (FR); Rosa Maria Rodriguez-Sarmiento, Basel (CH); Franz Schuler, Riehen (CH)

(73) Assignee: Hoffman-La Roche Inc., Nutley, NJ (US)

( * ) Notice: Subject to any disclaimer, the term of this patent is extended or adjusted under 35 U.S.C. 154(b) by 607 days.

(21) Appl. No.: 11/251,509

(22) Filed: Oct. 14, 2005

(65) Prior Publication Data

US 2006/0084679 A1    Apr. 20, 2006

(30) Foreign Application Priority Data

Oct. 19, 2004    (EP) .................................. 04105145

(51) Int. Cl.
*C07D 215/38*    (2006.01)
(52) U.S. Cl. ..................... 546/169; 514/314
(58) Field of Classification Search ................. 546/169; 514/314
See application file for complete search history.

(56) References Cited

U.S. PATENT DOCUMENTS 5,441,963 A    8/1995    McDonals et al.
7,098,222 B2 *    8/2006    Altenbach et al. ........... 514/314
2004/0152704 A1    8/2004    Altenbach et al.

FOREIGN PATENT DOCUMENTS

WO    WO 02/076925 A2    10/2002
WO    WO 02/092571 A1    11/2002

OTHER PUBLICATIONS

Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
Inagaki et al., J. Comp. Neurol 1988, 273, 283-300.

* cited by examiner

*Primary Examiner*—D. Margaret Seaman
(74) *Attorney, Agent, or Firm*—George W. Johnston; Dennis P. Tramaloni; Samuel H. Megerditchian

(57) ABSTRACT

The present invention relates to compounds of formula I:

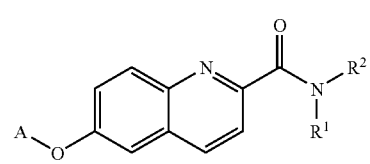

and pharmaceutically acceptable salts thereof as well as to pharmaceutical compositions comprising these compounds and to methods for their preparation. The compounds are useful for the treatment and/or prevention of diseases which are associated with the modulation of H3 receptors.

20 Claims, No Drawings

QUINOLINE DERIVATIVES AS H3R INVERSE AGONISTS

PRIORITY TO RELATED APPLICATIONS

This application claims the benefit of European Application No. 04105145.9, filed Oct. 19, 2004, which is hereby incorporated by reference in its entirety.

FIELD OF THE INVENTION

The present invention is directed to novel quinoline derivatives, their manufacture, pharmaceutical compositions containing them and their use as medicaments. The active compounds of the present invention are useful in treating obesity and other disorders. In particular, the present invention relates to compounds of the general formula

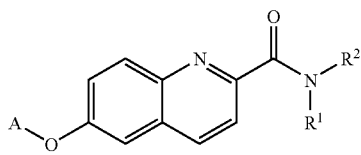

and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND OF THE INVENTION

Histamine (2-(4-imidazolyl) ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the central nervous system (CNS) and in the periphery through four distinct histamine receptors, the histamine H1, H2, H3 and H4 receptors.

H3 receptors are predominantly localized in the CNS. As an autoreceptor, H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release.

Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990,33, 4-11).

There is, therefore, a need for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In one embodiment of the present invention, provided is a compound of the formula I,

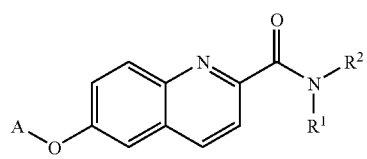

wherein:
$R^1$ is selected from the group consisting of hydrogen,
lower alkyl, lower alkenyl,
cycloalkyl, lower cycloalkylalkyl, wherein the cycloalkyl ring may be unsubstituted or substituted by one or two groups selected from the group consisting of lower alkyl, lower hydroxyalkyl and
lower alkoxyalkyl,
lower hydroxyalkyl,
lower alkoxyalkyl, and
lower heterocyclylalkyl, wherein the heterocyclyl ring may be unsubstituted or substituted by one or two groups selected from lower alkyl and halogen;
$R^2$ is selected from the group consisting of hydrogen,
lower alkyl, lower alkenyl, cycloalkyl, lower cycloalkylalkyl, wherein the cycloalkyl ring may be unsubstituted or substituted by one or two groups selected from the group consisting of lower alkyl, lower hydroxyalkyl and
lower alkoxyalkyl,
lower hydroxyalkyl,
lower alkoxyalkyl, and
lower heterocyclylalkyl, wherein the heterocyclyl ring may be unsubstituted or substituted by one or two groups selected from lower alkyl and halogen; or
$R^1$ and $R^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring being unsubstituted or substituted by one, two or three groups independently selected from the group consisting of lower alkyl, halogen, halogenalkyl, cyano, hydroxy, hydroxyalkyl, lower alkoxy, oxo, phenyl, benzyl, pyridyl and carbamoyl;

A is selected from

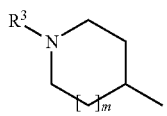

A1

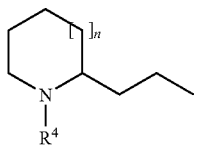

A2 or

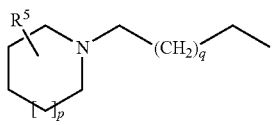

A3 wherein
m is 0, 1 or 2;
$R^3$ is lower alkyl;
n is 0, 1 or 2;
$R^7$ is lower alkyl;
p is 0, 1 or 2;
q is 0, 1 or 2;
$R^5$ is hydrogen or lower alkyl;
and pharmaceutically acceptable salts thereof.

In another embodiment of the present invention, provided is a process for the manufacture of a compound according to formula I, comprising the steps of: reacting a compound of the formula II

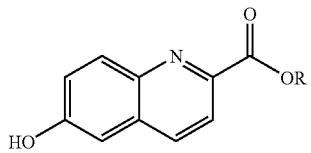

II wherein R is lower alkyl,
with an alcohol of the formula III

 HO-A

III wherein A is as defined in claim 1, in the presence of a trialkylphosphine or triphenylphosphine and of a diazo compound to obtain a compound of the formula IV

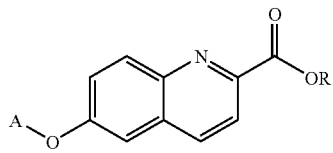

IV and converting the ester of formula IV into the acid of formula V

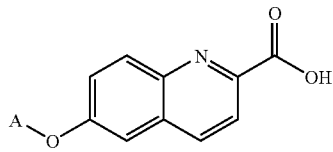

V under acidic or basic conditions,
and coupling the compound of formula V with an amine of the formula VI

 H—NR$^1$R$^2$

VI wherein $R^1$ and $R^2$ are as defined in claim 1, with the help of an coupling agent under basic conditions to obtain a compound of the formula I

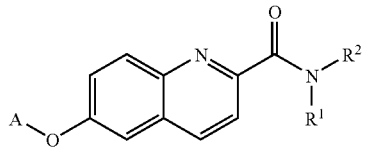

I wherein A, $R^1$ and $R^2$ are as defined in claim 1,
and if desired,
converting the compound obtained into a pharmaceutically acceptable salt.

In a further embodiment of the present invention, provided is a pharmaceutical composition comprising a therapeutically effective amount of a compound according to formula I and a pharmaceutically acceptable carrier and/or adjuvant.

In a yet another embodiment of the present invention, provided is a method for the treatment and/or prevention of diseases which are associated with the modulation of H3 receptors, comprising the step of administering a therapeutically effective amount of a compound according to formula I to a human being or animal in need thereof.

BACKGROUND OF THE INVENTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "lower alkenyl" or "$C_2$-$C_8$-alkenyl", alone or in combination, signifies a straight-chain or branched alkyl group comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "alkoxy" refers to the group R'—O—, wherein R' is alkyl. The term "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.butoxy, preferably methoxy and ethoxy and most preferred methoxy.

The term "lower alkoxyalkyl" or "alkoxy-$C_1$-$C_8$-alkyl" refers to lower alkyl groups as defined above wherein at least one of the hydrogen atoms of the lower alkyl group is replaced by an alkoxy group as defined above. Among the preferred lower alkoxyalkyl groups are methoxymethyl, methoxyethyl and ethoxymethyl, with methoxymethyl being especially preferred.

The term "halogen" refers to fluorine, chlorine, bromine and iodine, with fluorine, chlorine and bromine being preferred.

The term "lower halogenalkyl" or "halogen-$C_1$-$C_8$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_1$-$C_8$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_1$-$C_8$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "cycloalkyl" or "$C_3$-$C_7$-cycloalkyl" means a cycloalkyl ring containing 3 to 7 carbon atoms, such as cyclopropyl, cyclobutyl, cyclopentyl, cyclohexyl or cycloheptyl. The cycloalkyl ring may be optionally substituted as defined herein. Especially preferred is cyclopropyl.

The term "lower cycloalkylalkyl" or "$C_3$-$C_7$-cycloalkyl-$C_1$-$C_8$-alkyl" refers to lower alkyl groups as defined above wherein at least one of the hydrogen atoms of the lower alkyl group is replaced by a cycloalkyl group as defined above. Examples of preferred lower cycloalkylalkyl groups are cyclopropylmethyl or cyclopropylmethyl wherein the cyclopropyl group is substituted by lower alkyl, lower hydroxyalkyl or lower alkoxyalkyl, preferably methoxymethyl.

The term "heterocyclyl" means a monovalent saturated or partly unsaturated ring incorporating one, two, or three heteroatoms chosen from nitrogen, oxygen or sulfur. The heterocyclyl ring may be optionally substituted as defined herein. Examples of heterocyclyl moieties include azetidinyl, oxetanyl, pyrrolidinyl, imidazolidinyl, pyrazolidinyl, oxazolidinyl, isoxazolidinyl, thiazolidinyl, isothiazolidinyl, dihydropyridyl, piperidyl, piperazinyl, morpholinyl, or thiomorpholinyl, azepinyl, dihydropyrrolyl, pyrrolidinyl, pyrazolidinyl, imidazolinyl, dihydrofuryl, tetrahydrofuryl, dihydropyranyl or tetrahydropyranyl. Especially preferred are oxetanyl, piperidyl and morpholinyl.

The term "lower heterocyclylalkyl" or "heterocyclyl-$C_1$-$C_8$-alkyl" refers to lower alkyl groups as defined above wherein at least one of the hydrogen atoms of the lower alkyl group is replaced by a heterocyclyl group as defined above. An examples of a preferred lower heterocyclylalkyl group is 3-fluorooxetan-3-yl.

The term "a 4-, 5-, 6- or 7-membered saturated or partly unsaturated heterocyclic ring optionally containing a further heteroatom selected from nitrogen, oxygen or sulfur" refers to a saturated or partly unsaturated N-heterocyclic ring, which may optionally contain a further nitrogen, oxygen or sulfur atom, such as 2,5-dihydropyrrolidinyl, pyrrolidinyl, imidazolidinyl, pyrazolidinyl, oxazolidinyl, isoxazolidinyl, thiazolidinyl, isothiazolidinyl, piperidyl, piperazinyl, morpholinyl, thiomorpholinyl, or 3,6-dihydro-2H-pyridinyl. The heteroyclic ring may be unsubstituted or substituted by one, two or three groups independently selected from lower alkyl, lower alkoxy and halogen.

The term "carbamoyl" refers to the group —CO—NH$_2$.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

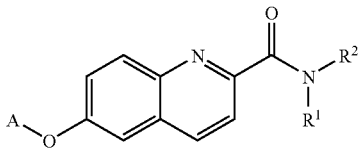

I wherein
R¹ is selected from the group consisting of hydrogen,
lower alkyl, lower alkenyl,
cycloalkyl or lower cycloalkylalkyl, wherein the cycloalkyl ring may be unsubstituted or substituted by one or two groups selected from the group consisting of lower alkyl, lower hydroxyalkyl and lower alkoxyalkyl,
lower hydroxyalkyl,
lower alkoxyalkyl, and
lower heterocyclylalkyl, wherein the heterocyclyl ring may be unsubstituted or substituted by one or two groups selected from lower alkyl and halogen;
R² is selected from the group consisting of hydrogen,
lower alkyl, lower alkenyl,
cycloalkyl or lower cycloalkylalkyl, wherein the cycloalkyl ring may be unsubstituted or substituted by one or two groups selected from the group consisting of lower alkyl, lower hydroxyalkyl and lower alkoxyalkyl,
lower hydroxyalkyl,
lower alkoxyalkyl, and
lower heterocyclylalkyl, wherein the heterocyclyl ring may be unsubstituted or substituted by one or two groups selected from lower alkyl and halogen; or
R¹ and R² together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring being unsubstituted or substituted by one, two or three groups independently selected from the group consisting of lower alkyl, halogen, halogenalkyl, cyano, hydroxy, hydroxyalkyl, lower alkoxy, oxo, phenyl, benzyl, pyridyl and carbamoyl;

A is selected from

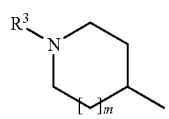

A1

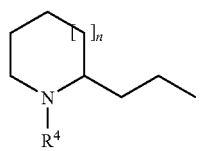

A2 or

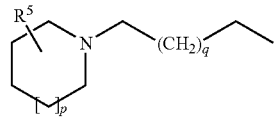

A3 wherein
m is 0, 1 or 2;
R³ is lower alkyl;
n is 0, 1 or 2;
R⁷ is lower alkyl;
p is 0, 1 or 2;
q is 0, 1 or 2;
R⁵ is hydrogen or lower alkyl;
and pharmaceutically acceptable salts thereof.

Preferred compounds of formula I according to the present invention are those, wherein R¹ is selected from the group consisting of hydrogen, lower alkyl, lower alkenyl, cycloalkyl, lower cycloalkylalkyl, wherein the cycloalkyl ring may be unsubstituted or substituted by one or two groups selected from lower alkyl, lower hydroxyalkyl or lower alkoxyalkyl, lower hydroxyalkyl, lower alkoxyalkyl, and lower heterocyclylalkyl, wherein the heterocyclyl ring may be unsubstituted or substituted with one or two groups selected from lower alkyl or halogen, and R² is hydrogen or lower alkyl.

More preferred are compounds of formula I according to present invention, wherein R¹ is selected from the group consisting of lower alkyl, cycloalkyl, lower cycloalkylalkyl, wherein the cycloalkyl ring may be unsubstituted or substituted by lower alkoxyalkyl, lower alkoxyalkyl, and lower heterocyclylalkyl wherein the heterocyclyl ring may be unsubstituted or substituted with one or two groups selected from lower alkyl or halogen, and R² is hydrogen or lower alkyl.

Especially preferred are those compounds of formula I, wherein R¹ and R² are lower alkyl.

Another group of preferred compounds of formula I according to present invention are those, wherein R¹ and R² together with the nitrogen atom to which they are attached form a 4-, 5-, 6- or 7-membered saturated or partly unsaturated heterocyclic ring optionally containing a further heteroatom selected from nitrogen, oxygen or sulfur, said heterocyclic ring being unsubstituted or substituted by one, two or three groups independently selected from lower alkyl, halogen, halogenalkyl, cyano, hydroxy, hydroxyalkyl, lower alkoxy, oxo, phenyl, benzyl, pyridyl and carbamoyl.

Preferred compounds of formula I are those, wherein R¹ and R² together with the nitrogen atom to which they are attached form a 4-, 5-, 6- or 7-membered saturated or partly unsaturated heterocyclic ring optionally containing a further heteroatom selected from nitrogen, oxygen or sulfur, said heterocyclic ring being unsubstituted or substituted by one, two or three groups independently selected from lower alkyl, halogen, halogenalkyl, cyano, hydroxy, lower alkoxy, oxo, phenyl, benzyl, pyridyl and carbamoyl.

More preferred are those compounds of formula I, wherein R¹ and R² together with the nitrogen atom to which they are attached form a 4-, 5-, or 6- or 7-membered saturated or partly unsaturated heterocyclic ring optionally containing a further heteroatom selected from nitrogen, oxygen or sulfur, said heterocyclic ring being unsubstituted or substituted by one, two or three groups independently selected from lower alkyl, halogen, halogenalkyl, cyano, hydroxy, lower alkoxy, and oxo.

Even more preferred are compounds of formula I, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenalkyl, cyano, hydroxy, lower alkoxy, and oxo.

Especially preferred are compounds of formula I, wherein $R^1$ and $R^2$ together with the nitrogen atom to which they are attached form a heterocyclic ring selected from morpholinyl, thiomorpholinyl, 1,1-dioxothiomorpholinyl, 3,6-dihydro-2H-pyridinyl, piperidinyl, 2-methylpiperidinyl, 3-methylpiperidinyl, 4-hydroxypiperidinyl, 4,4-difluoropiperidinyl, 2,5-dihydropyrrolyl, 4-methylpiperidinyl, pyrrolidinyl, 2-methylpyrrolidinyl, 2-trifluoromethylpyrrolidinyl, 2-cyanopyrrolidinyl, 3-hydroxypyrrolidinyl and azetidinyl.

Furthermore, compounds of formula I according to the present invention, wherein A signifies

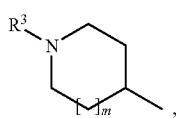

and wherein m is 0, 1 or 2, and $R^3$ is lower alkyl, are preferred.

Within this group, those compounds of formula I are preferred, wherein m is 0, thus meaning pyrrolidine groups are preferred.

A further preferred group includes those compounds of formula I, wherein m is 1, thus meaning piperidine groups are also preferred.

Also preferred are compounds of formula I according to the present invention, wherein A signifies

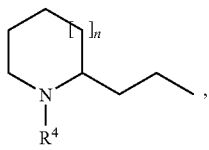

and wherein n is 0, 1 or 2; and $R^4$ is lower alkyl, with those compounds, wherein n is 0, thus meaning pyrrolidine derivatives, being more preferred.

Further preferred compounds of formula I according to the present invention are those, wherein A signifies

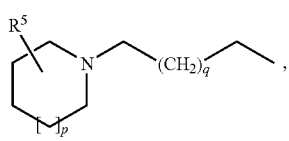

wherein p is 0, 1 or 2, q is 0, 1 or 2, and $R^5$ is hydrogen or lower alkyl.

Within this group, those compounds of formula I are preferred, wherein p is 1, thus meaning piperidine groups are preferred. Especially preferred are those compounds of formula I, wherein p is 1 and q is 1.

Furthermore, compounds wherein $R^5$ is hydrogen, are preferred.

Examples of preferred compounds of formula I are the following:

[6-(1-isopropyl-piperidin-4-yloxy)-quinolin-2-yl]-(4-methoxy-piperidin-1-yl)-methanone,
(2,5-dihydro-pyrrol-1-yl)-[6-(1-isopropyl-piperidin-4-yloxy)-quinolin-2-yl]-methanone,
6-(1-isopropyl-piperidin-4-yloxy)-quinoline-2-carboxylic acid ethyl-methyl-amide,
[6-(1-isopropyl-piperidin-4-yloxy)-quinolin-2-yl]-(2-methyl-pyrrolidin-1-yl)-methanone,
6-(1-isopropyl-piperidin-4-yloxy)-quinoline-2-carboxylic acid tert-butylamide,
6-(1-isopropyl-piperidin-4-yloxy)-quinoline-2-carboxylic acid cyclopropylmethyl-propyl-amide,
[6-(1-isopropyl-piperidin-4-yloxy)-quinolin-2-yl]-(2-methyl-piperidin-1-yl)-methanone,
(4-hydroxy-piperidin-1-yl)-[6-(1-isopropyl-piperidin-4-yloxy)-quinolin-2-yl]-methanone,
[6-(1-isopropyl-piperidin-4-yloxy)-quinolin-2-yl]-(3-methyl-piperidin-1-yl)-methanone,
(3,4-dihydro-1H-isoquinolin-2-yl)-[6-(3-piperidin-1-yl-propoxy)-naphthalen-2-yl]-methanone 1:1 hydrochloride,
[6-(1-isopropyl-piperidin-4-yloxy)-quinolin-2-yl]-thiomorpholin-4-yl-methanone,
[6-(1-isopropyl-piperidin-4-yloxy)-quinolin-2-yl]-(2-trifluoromethyl-pyrrolidin-1-yl)-methanone,
6-(1-isopropyl-piperidin-4-yloxy)-quinoline-2-carboxylic acid ethyl-(2-methoxy-ethyl)-amide,
azetidin-1-yl-[6-(1-isopropyl-piperidin-4-yloxy)-quinolin-2-yl]-methanone,
(3,6-dihydro-2H-pyridin-1-yl)-[6-(1-isopropyl-piperidin-4-yloxy)-quinolin-2-yl]-methanone,
6-(1-isopropyl-piperidin-4-yloxy)-quinoline-2-carboxylic acid (3-fluoro-oxetan-3-ylmethyl)-amide,
6-(1-isopropyl-piperidin-4-yloxy)-quinoline-2-carboxylic acid (1-methoxymethyl-cyclopropylmethyl)-amide,
{6-(1-isopropyl-piperidin-4-yloxy)-quinoline-2-carboxylic acid [2-(tetrahydro-pyran-4-yl)-ethyl]-amide,
[6-(1-isopropyl-piperidin-4-yloxy)-quinolin-2-yl]-morpholin-4-yl-methanone,
6-(1-isopropyl-piperidin-4-yloxy)-quinoline-2-carboxylic acid cyclohexyl-methyl-amide,
(4,4-difluoro-piperidin-1-yl)-[6-(1-isopropyl-piperidin-4-yloxy)-quinolin-2-yl]-methanone,
(3-hydroxy-pyrrolidin-1-yl)-[6-(1-isopropyl-piperidin-4-yloxy)-quinolin-2-yl]-methanone,
[6-(1-isopropyl-piperidin-4-yloxy)-quinolin-2-yl]-pyrrolidin-1-yl-methanone,
(R)-1-[6-(1-isopropyl-piperidin-4-yloxy)-quinoline-2-carbonyl]-pyrrolidine-2-carbonitrile,
(1,1-dioxo-thiomorpholin-4-yl)-[6-(1-isopropyl-piperidin-4-yloxy)-quinolin-2-yl]-methanone,
6-(1-isopropyl-piperidin-4-yloxy)-quinoline-2-carboxylic acid dimethylamide
(2,5-dihydro-pyrrol-1-yl)-[6-(1-isopropyl-pyrrolidin-3-yloxy)-quinolin-2-yl]-methanone,
([6-(1-isopropyl-pyrrolidin-3-yloxy)-quinolin-2-yl]-(4-methoxy-piperidin-1-yl)-methanone,
6-(1-isopropyl-pyrrolidin-3-yloxy)-quinoline-2-carboxylic acid ethyl-methyl-amide, ([6-(1-isopropyl-pyrrolidin-3-yloxy)-quinolin-2-yl]-(4-methyl-piperidin-1-yl)-methanone,
[6-(1-isopropyl-pyrrolidin-3-yloxy)-quinolin-2-yl]-(2-methyl-pyrrolidin-1-yl)-methanone,
6-(1-isopropyl-pyrrolidin-3-yloxy)-quinoline-2-carboxylic acid tert-butylamide,
6-(1-isopropyl-pyrrolidin-3-yloxy)-quinoline-2-carboxylic acid cyclopropylmethyl-propyl-amide,
{[6-(1-isopropyl-pyrrolidin-3-yloxy)-quinolin-2-yl]-(2-methyl-piperidin-1-yl)-methanone,
[6-(1-isopropyl-pyrrolidin-3-yloxy)-quinolin-2-yl]-(3-methyl-piperidin-1-yl)-methanone,
6-(1-isopropyl-pyrrolidin-3-yloxy)-quinoline-2-carboxylic acid isopropyl-methyl-amide,
[6-(1-isopropyl-pyrrolidin-3-yloxy)-quinolin-2-yl]-thiomorpholin-4-yl-methanone,
[6-(1-isopropyl-pyrrolidin-3-yloxy)-quinolin-2-yl]-(2-trifluoromethyl-pyrrolidin-1-yl)-methanone,
6-(1-isopropyl-pyrrolidin-3-yloxy)-quinoline-2-carboxylic acid ethyl-(2-methoxy-ethyl)-amide,
azetidin-1-yl-[6-(1-isopropyl-pyrrolidin-3-yloxy)-quinolin-2-yl]-methanone,
(3,6-dihydro-2H-pyridin-1-yl)-[6-(1-isopropyl-pyrrolidin-3-yloxy)-quinolin-2-yl]-methanone,
6-(1-isopropyl-pyrrolidin-3-yloxy)-quinoline-2-carboxylic acid (3-fluoro-oxetan-3-ylmethyl)-amide,
6-(1-isopropyl-pyrrolidin-3-yloxy)-quinoline-2-carboxylic acid (1-methoxymethyl-cyclopropylmethyl)-amide,
6-(1-isopropyl-pyrrolidin-3-yloxy)-quinoline-2-carboxylic acid [2-(tetrahydro-pyran-4-yl)-ethyl]-amide,
(4,4-difluoro-piperidin-1-yl)-[6-(1-isopropyl-pyrrolidin-3-yloxy)-quinolin-2-yl]-methanone,
[6-(1-isopropyl-piperidin-4-yloxy)-quinolin-2-yl]-morpholin-4-yl-methanone,
(4-methoxy-piperidin-1-yl)-[6-(3-piperidin-1-yl-propoxy)-quinolin-2-yl]-methanone,
(4-methyl-piperidin-1-yl)-[6-(3-piperidin-1-yl-propoxy)-quinolin-2-yl]-methanone
morpholin-4-yl-[6-(3-piperidin-1-yl-propoxy)-quinolin-2-yl]-methanone,
(2-methyl-pyrrolidin-1-yl)-[6-(3-piperidin-1-yl-propoxy)-quinolin-2-yl]-methanone,
6-(3-piperidin-1-yl-propoxy)-quinoline-2-carboxylic acid cyclopropylmethyl-propyl-amide,
[6-(3-piperidin-1-yl-propoxy)-quinolin-2-yl]-(2-trifluoromethyl-pyrrolidin-1-yl)-methanone,
(2,5-dihydro-pyrrol-1-yl)-[6-(3-piperidin-1-yl-propoxy)-quinolin-2-yl]-methanone,
6-(3-piperidin-1-yl-propoxy)-quinoline-2-carboxylic acid ethyl-(2-methoxy-ethyl)-amide,
azetidin-1-yl-[6-(3-piperidin-1-yl-propoxy)-quinolin-2-yl]-methanone,
(3,6-dihydro-2H-pyridin-1-yl)-[6-(3-piperidin-1-yl-propoxy)-quinolin-2-yl]-methanone,
(4,4-difluoro-piperidin-1-yl)-[6-(3-piperidin-1-yl-propoxy)-quinolin-2-yl]-methanone,
6-(3-piperidin-1-yl-propoxy)-quinoline-2-carboxylic acid cyclohexyl-methyl-amide,
6-(3-piperidin-1-yl-propoxy)-quinoline-2-carboxylic acid (1-methoxymethyl-cyclopropylmethyl)-amide,
6-(3-piperidin-1-yl-propoxy)-quinoline-2-carboxylic acid (3-fluoro-oxetan-3-ylmethyl)-amide,
6-(3-piperidin-1-yl-propoxy)-quinoline-2-carboxylic acid [2-(tetrahydro-pyran-4-yl)-ethyl]-amide,
6-(3-piperidin-1-yl-propoxy)-quinoline-2-carboxylic acid (tetrahydro-pyran-4-yl)-amide,
(2-methyl-piperidin-1-yl)-[6-(3-piperidin-1-yl-propoxy)-quinolin-2-yl]-methanone,
[6-(3-piperidin-1-yl-propoxy)-quinolin-2-yl]-pyrrolidin-1-yl-methanone,
(R)-1-[6-(3-piperidin-1-yl-propoxy)-quinoline-2-carbonyl]-pyrrolidine-2-carbonitrile,
(1,1-dioxo-thiomorpholin-4-yl)-[6-(3-piperidin-1-yl-propoxy)-quinolin-2-yl]-methanone,
(4-methyl-piperidin-1-yl)-{6-[2-(1-methyl-pyrrolidin-2-yl)-ethoxy]-quinolin-2-yl}-methanone,
{6-[2-(1-methyl-pyrrolidin-2-yl)-ethoxy]-quinolin-2-yl}-pyrrolidin-1-yl-methanone,
(R)-1-{6-[2-(1-methyl-pyrrolidin-2-yl)-ethoxy]-quinoline-2-carbonyl}-pyrrolidine-2-carbonitrile,
(1,1-dioxo-thiomorpholin-4-yl)-{6-[2-(1-methyl-pyrrolidin-2-yl)-ethoxy]-quinolin-2-yl}-methanone,
(4-methoxy-piperidin-1-yl)-{6-[2-(1-methyl-pyrrolidin-2-yl)-ethoxy]-quinolin-2-yl}-methanone,
{6-[2-(1-methyl-pyrrolidin-2-yl)-ethoxy]-quinolin-2-yl}-morpholin-4-yl-methanone,
azetidin-1-yl-{6-[2-(1-methyl-pyrrolidin-2-yl)-ethoxy]-quinolin-2-yl}-methanone,
6-[2-(1-methyl-pyrrolidin-2-yl)-ethoxy]-quinoline-2-carboxylic acid [2-(tetrahydro-pyran-4-yl)-ethyl]-amide,
6-[2-(1-methyl-pyrrolidin-2-yl)-ethoxy]-quinoline-2-carboxylic acid (3-fluoro-oxetan-3-ylmethyl)-amide,
(2-methyl-pyrrolidin-1-yl)-{6-[2-(1-methyl-pyrrolidin-2-yl)-ethoxy]-quinolin-2-yl}-methanone,
(S)-1-[6-(1-isopropyl-piperidin-4-yloxy)-quinoline-2-carbonyl]-pyrrolidine-2-carbonitrile,
[6-(1-isopropyl-piperidin-4-yloxy)-quinolin-2-yl]-(4-methyl-piperidin-1-yl)-methanone,
(4-hydroxymethyl-piperidin-1-yl)-[6-(1-isopropyl-piperidin-4-yloxy)-quinolin-2-yl]-methanone,
6-(1-isopropyl-piperidin-4-yloxy)-quinoline-2-carboxylic acid isobutyl-amide,
6-(1-isopropyl-pyrrolidin-3-yloxy)-quinoline-2-carboxylic acid cyclohexyl-methyl-amide, and pharmaceutically acceptable salts thereof.

Particularly preferred compounds of formula I of the present invention are the following:
[6-(1-isopropyl-piperidin-4-yloxy)-quinolin-2-yl]-(4-methoxy-piperidin-1-yl)-methanone,
[6-(1-isopropyl-piperidin-4-yloxy)-quinolin-2-yl]-(2-methyl-pyrrolidin-1-yl)-methanone,
[6-(1-isopropyl-piperidin-4-yloxy)-quinolin-2-yl]-(2-trifluoromethyl-pyrrolidin-1-yl)-methanone,
azetidin-1-yl-[6-(1-isopropyl-piperidin-4-yloxy)-quinolin-2-yl]-methanone,
6-(1-isopropyl-piperidin-4-yloxy)-quinoline-2-carboxylic acid (3-fluoro-oxetan-3-ylmethyl)-amide,
6-(1-isopropyl-piperidin-4-yloxy)-quinoline-2-carboxylic acid (1-methoxymethyl-cyclopropylmethyl)-amide,
[6-(1-isopropyl-piperidin-4-yloxy)-quinolin-2-yl]-pyrrolidin-1-yl-methanone,
(R)-1-[6-(1-isopropyl-piperidin-4-yloxy)-quinoline-2-carbonyl]-pyrrolidine-2-carbonitrile,
azetidin-1-yl-[6-(3-piperidin-1-yl-propoxy)-quinolin-2-yl]-methanone,
(R)-1-[6-(3-piperidin-1-yl-propoxy)-quinoline-2-carbonyl]-pyrrolidine-2-carbonitrile,
(S)-1-[6-(1-isopropyl-piperidin-4-yloxy)-quinoline-2-carbonyl]-pyrrolidine-2-carbonitrile, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartrate, and methanesulphonate.

Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

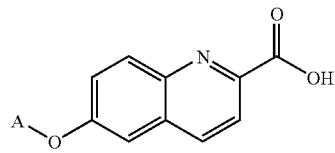

wherein R is lower alkyl, with an alcohol of the formula III

HO-A    III wherein A is as defined herein before, in the presence of a trialkylphosphine or triphenylphosphine and of a diazo compound to obtain a compound of the formula IV

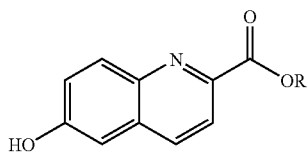

and converting the ester of formula IV into the acid of formula V

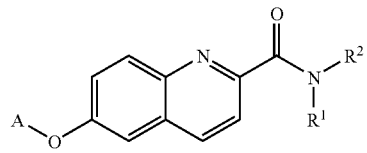

under acidic or basic conditions, and coupling the compound of formula V with an amine of the formula VI

H—NR$^1$R$^2$    VI wherein R$^1$ and R$^2$ are as defined herein before, with the help of an coupling agent under basic conditions to obtain a compound of the formula I

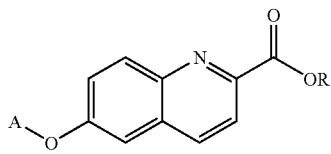

wherein A, R$^1$ and R$^2$ are as defined herein before, and if desired, converting the compound obtained into a pharmaceutically acceptable salt.

Coupling agents for the reaction of compounds of formula V with amines of formula VI are for example N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), or O-benzotriazol-1-yl-N,N,N',N'-tetramethyluronium tetrafluoroborate (TBTU).

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Scheme 1

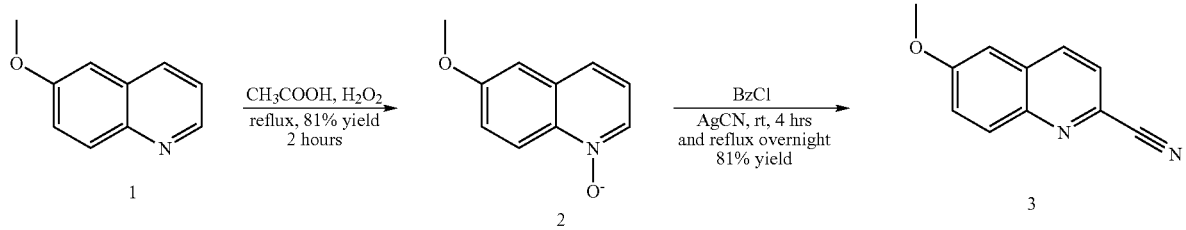

-continued

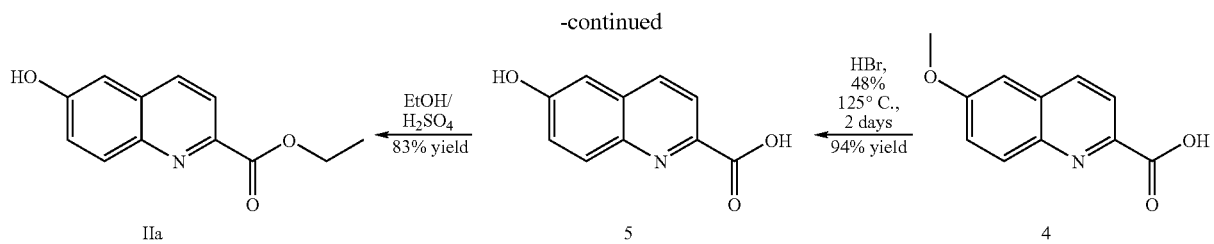

Compounds of formula II can be manufactured starting from commercially available 6-methoxy-quinoline (1) that can converted to the N-oxide 2 by reaction with hydrogen peroxide and a solvent like acetic acid under refluxing conditions. The 6-methoxy-quinoline-1-oxide is reacted with silver cyanide and benzoyl chloride to obtain the 6-methoxy-quinoline-2-carbonitrile 3 via a modification of the Reisset'sche reaction (Ber., 38, 1610 (1905). Hydrolysis of the cyano group can be affected by employing an acidic or basic medium. We find it convenient to use a base like sodium hydroxide and after acidic treatment of the mixture we obtained the corresponding 6-methoxy-quinoline-2-carboxylic acid 4. Removal of the methyl group with an acid like hydrobromic acid 48% in water gives 6-hydroxy-quinoline-2-carboxylic acid (5). The acid can be esterified with an alcohol like ethanol and an acid like sulfuric acid to yield the 6-hydroxy-quinoline-2-carboxylic acid ester II, for example 6-hydroxy-quinoline-2-carboxylic acid ethyl ester (IIa).

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given above unless indicated to the contrary.

Compounds of general formula I can be prepared according to scheme 2 as follows:

a) The syntheses of ethers are widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, 1999). The transformation can be affected by employing reaction conditions which are commonly utilised in the so called "Mitsunobu reaction" which is known to those in the art and widely described (Hughes, David L. The Mitsunobu reaction. Organic Reactions (John Wiley & Sons, New York, 1992, 42, 335-656) We find it convenient to couple an ester of formula II with alcohols of formula III (either commercially available or accessible by methods described in references or by methods known in the art; as appropriate) under conditions employing a phosphine like a trialkylphosphine such as tributylphosphine ($(n-Bu)_3P$), triphenylphosphine ($Ph_3P$) and the like and a diazo-compound like diethyl-azodicarboxylate (DEAD), diisopropyl-azodicarboxylate (DIAD) (optionally polymer bound), tetramethyl azodicarboxamide and the like in a solvent commonly used in such transformations like tetrahydrofurane (THF), toluene, dichloromethane and the like. There is no particular restriction on the nature of the solvent to be employed, provided that it has no adverse effect on the reaction or the reagents involved and that it can dissolve the reagents, at least to some extent. The reaction

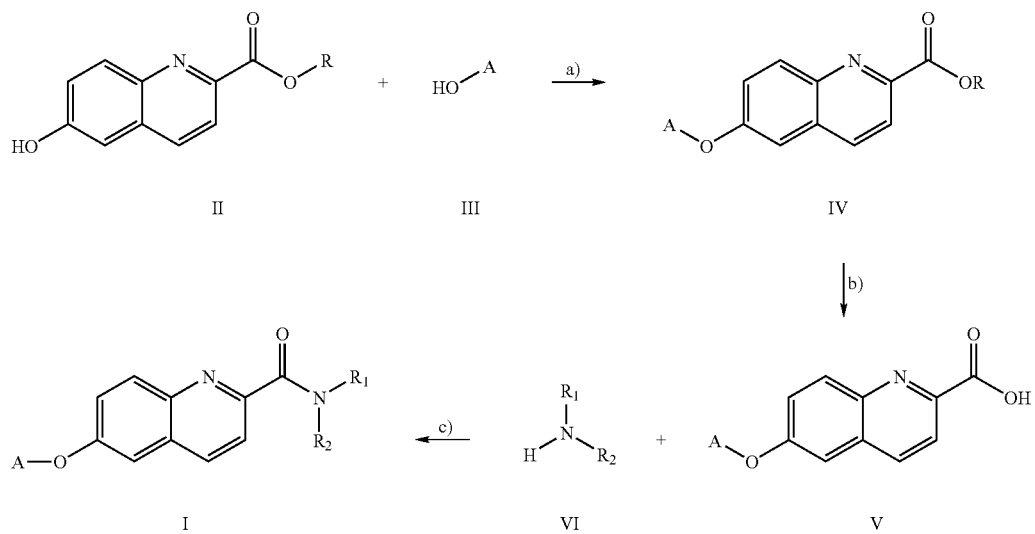

Scheme 2 can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the compounds of formula IV.

b) The hydrolysis of esters are widely described in literature and the procedures are known to those in the art (For reaction conditions described in literature affecting such reactions see for example:). The transformation can be affected by employing acidic or basic medium. We find it convenient to use acidic conditions employing an acid like HCl and a solvent like dioxane, THF and the like. There is no particular restriction on the nature of the solvent to be employed, provided that it has no adverse effect on the reaction or the reagents involved and that it can dissolve the reagents, at least to some extent. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the title compounds VI.

c) The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, 1999). 6-Alkoxy-quinoline-2-carboxylic acids of formula IV can conveniently be transformed to the respective amide through coupling with an amine V (either commercially available or accessible by methods described in references or by methods known in the art; as appropriate) by employing the usage of coupling agents. For example coupling agents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally Well be employed to affect such transformation. We find it convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives of formula I.

As described above, the compounds of formula I of the present invention can be used as medicaments for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use as medicament for the treatment and/or prevention of obesity is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In another embodiment, the invention relates to a method for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastrointestinal disorders. A method for the treatment and/or prevention of obesity is preferred.

The invention further relates to the use of compounds of formula I as defined above for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the treatment and/or prevention of obesity is preferred.

In addition, the invention relates to the use of compounds of formula I as defined above for the preparation of medicaments for the treatment and/or prevention of diseases which are associated with the modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders. The use of compounds of formula I as defined above for the preparation of medicaments for the treatment and/or prevention of obesity is preferred.

The compounds of formula I and their pharmaceutically acceptable salts possess valuable pharmacological properties. Specifically, it has been found that the compounds of the present invention are good histamine 3 receptor (H3R) antagonists and/or inverse agonists.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Intermediate 1

6-Hydroxy-quinoline-2-carboxylic acid ethyl ester a) 6-Methoxy-quinoline 1-oxide

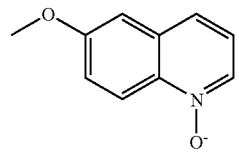

6-Methoxy quinoline (15 g, 0.094 mol) was dissolved in acetic acid (97 ml) and treated with hydrogen peroxide (37 ml). The mixture was stirred to 100° C. for 2 hours. After evaporation to dryness 100 ml of water was added to the residue until a precipitate appears. Filtration and washing with water gives a yellow precipitate that is dried under vacuum to yield 13.5 g of the title compound as a light yellow solid (82%). MS (m/e): 176.3 (M+H)$^+$.

b) 6-Methoxy-quinoline-2-carbonitrile

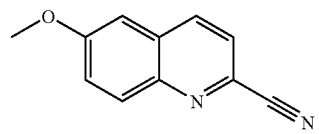

6-Methoxy-quinoline-1-oxide (13.48 g, 0.076 mol) in 30 ml chloroform was treated with 3.87 g (0.028 mol) of benzoyl chloride and 3.65 g (0.0 27 mol) of silver cyanide. The mixture was stirred for 4 hours at room temperature and stirred to reflux for additional 14 h. After evaporation of the solvent to half volume the mixture was cooled to 0° C. and a precipitate of silver salt appeared. The mixture was filtered and the solution was concentrated and the solid residue was washed in diethyl ether and dried under vacuum to yield 11 g (82%) of the title compound as light brown solid. MS (m/e)=185.3 (M+H)$^+$.

c) 6-Methoxy-quinoline-2-carboxylic acid

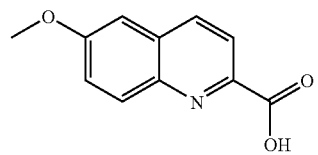

6-Methoxy-quinoline-2-carbonitrile (9.3 g, 0.050 mol) in 96 ml methanol was treated with 240 ml of 20% NaOH and the mixture was heated to 120° C. in a sealed tube overnight. After cooling to 0° C. a precipitate appeared. The mixture was filtered to get a sodium salt that was suspended in water. HCl 25% was added until pH 3-4 to get the acid as a precipitate that was filtered and dried under vacuum. The mother liquid of the first filtration was acidified with HCl 25% until pH 3-4 until a precipitate appeared. The precipitate was filtered and the solid was washed in water and dried under vacuum to yield 9.6 g (86%) of the title compound as light brown solid. MS (m/e)=204 (M+H)$^+$.

d) 6-Hydroxy-quinoline-2-carboxylic acid

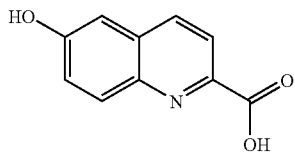

6-Methoxy-quinoline-2-carboxylic acid (4 g, 0.019 mol) was suspended in hydrobromic acid 48% in water (80 ml) and the mixture was heated at 125° C. overnight. After cooling to 0° C. ammonium hydroxide was added until the pH was 6-7 followed by addition of HCl until the pH was 3-4 and the compound precipitated. The solid was filtrated, washed with water and dried under vacuum to yield 3.5 g (0.0185 mol, 97% of theory) of the title compound as a yellow solid MS (m/e)=190.1 (M+H)$^+$.

e) 6-Hydroxy-quinoline-2-carboxylic acid ethyl ester

6-Hydroxy-quinoline-2-carboxylic acid (2.3 g, 0.012 mol) was dissolved in absolute ethanol (150 ml). Sulfuric acid (0.550 ml, 0.0096 mol) was added and the mixture was refluxed for 16 hours. After cooling to room temperature the ethanol was evaporated and 60 ml of ethyl acetate, 50 ml of cooled water were added. The pH was adjusted to 7 with solid NaHCO$_3$. Extraction and concentration of the organic phase gave the title product as a light yellow solid that was used for the next steps without purification (2.1 g, 81% of theory). MS (m/e)=218.4 (M+H)$^+$.

Intermediate 2

(6-(1-Isopropyl-piperidin-4-yloxy)-quinoline-2-carboxylic acid 1:1 hydrochloride a) 6-(1-Isopropyl-piperidin-4-yloxy)-quinoline-2-carboxylic acid ethyl ester

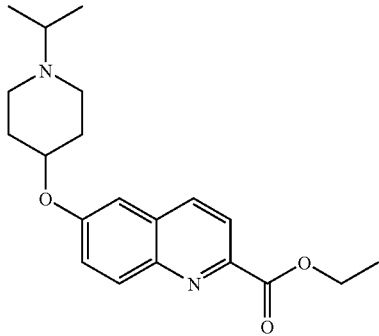

A mixture of 1 g (0.0046 mol) of 6-hydroxy-quinoline-2-carboxylic acid ethyl ester, 2.4 g (0.0092 mol) of triphenylphospine (Fluka), 2.4 g (0.0092 mol) of 1-isopropyl-piperidin-4-ol and 1.6 ml (0.0092 mol) of di-tert.-butyl azadicarboxylate 40% in toluene in 100 ml THF was stirred for a prolonged period of time at 35° C. The mixture was filtered through a pad of silica and washed with 30 ml THF. The mixture was evaporated to dryness and purified on silica eluting with a gradient of DCM/MeOH 98/2. The product fractions were evaporated and the residue was triturated with diethyl ether to yield after drying under vacuum 1.3 mg (83%) of the title compound as white solid. MS (m/e): 343.3 (M+H)$^+$.

b) 6-(1-Isopropyl-piperidin-4-yloxy)-quinoline-2-carboxylic acid 1:1 hydrochloride

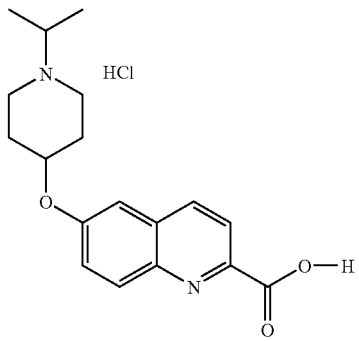

6-(1-Isopropyl-piperidin-4-yloxy)-quinoline-2-carboxylic acid ethyl ester (1.1 g, 0.0033 mol) was dissolved in dioxane (25 ml). HCl 37% (2.06 ml, 0.066 mol) was added and the mixture was stirred at 85° C. for 16 hours. Dioxane was evaporated and toluene (3×15 ml) was used to remove the remaining water by azeotropic distillation. After evaporation of the toluene the title compound was obtained as a yellow solid after drying under vacuum (1.3 g, 100% of theory). MS (m/e)=315.2 (M+H)$^+$.

Intermediate 3

6-(1-Isopropyl-pyrrolidin-3-yloxy)-quinoline-2-carboxylic acid acid 1:1 hydrochloride a) 6-(1-Isopropyl-pyrrolidin-3-yloxy)-quinoline-2-carboxylic acid ethyl ester

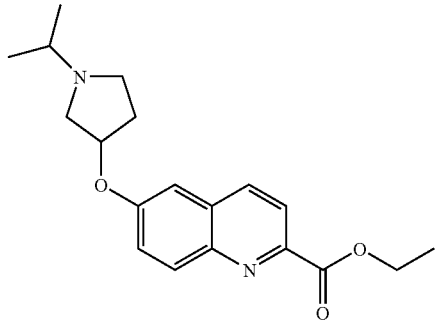

A mixture of 0.960 g (0.0044 mol) of 6-hydroxy-quinoline-2-carboxylic acid ethyl ester, 2.32 g (0.0088 mmol) of triphenylphospine (Fluka), 0.739 g (0.0057 mmol) of 1-isopropyl-3-pyrrolidinol and 1.61 ml (0.0088 mmol) of di-tert.-butyl azadicarboxylate 40% in toluene in 100 ml THF was stirred for a prolonged period of time at 35° C. The mixture was filtered through a pad of silica and washed with 30 ml of THF. The mixture was evaporated to dryness and purified on silica eluting with a gradient of DCM/MeOH 98/2. The product fractions were evaporated and the residue was triturated with diethyl ether to yield after drying under vacuum 1.35 g (94%) of the title compound as white solid. MS (m/e): 329.3 (M+H)$^+$.

b) 6-(1-Isopropyl-pyrrolidin-3-yloxy)-quinoline-2-carboxylic acid acid 1:1 hydrochloride

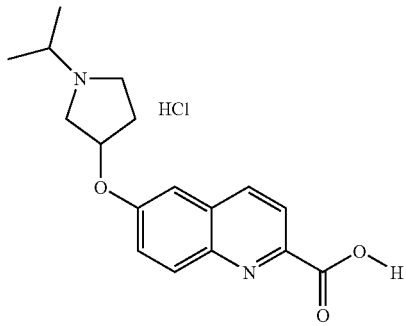

6-(1-Isopropyl-pyrrolidin-3-yloxy)-quinoline-2-carboxylic acid ethyl ester (0.5 g, 0.002 mol) was dissolved in dioxane (20 ml). HCl 37% (0.94 ml, 0.03 mol) was added and the mixture was stirred at 85° C. for 16 hours. Dioxane was evaporated and toluene (3×15 ml) was used to remove the remaining water by azeotropic distillation. After evaporation of the toluene the title compound was obtained as a yellow solid after drying under vacuum (0.570 g, 100% of theory). MS (m/e)=301.2 (M+H)$^+$.

Intermediate 4

6-(3-Piperidin-1-yl-propoxy)-quinoline-2-carboxylic acid 1:1 hydrochloride a) 6-(3-Piperidin-1-yl-propoxy)-quinoline-2-carboxylic acid ethyl ester

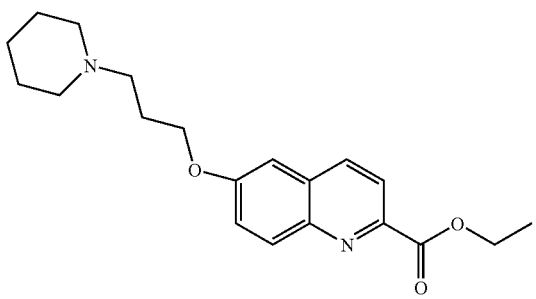

A mixture of 0.400 g (0.002 mol) of 6-hydroxy-quinoline-2-carboxylic acid ethyl ester, 0.966 g (0.004 mmol) of triphenylphospine (Fluka), 0.396 g (0.003 mmol) of 3-piperidin-1-yl-propan-1-ol and 0.68 ml (0.004 mmol) of di-tert.-butyl azadicarboxylate 40% in toluene in 40 ml THF was stirred for a prolonged period of time at 35° C. The mixture was filtered through a pad of silica and washed with 30 ml THF. The mixture was evaporated to dryness and purified on silica eluting with a gradient of DCM/MeOH/NH4OH from 97/3/0.5 to 90/10/0.5. The product fractions were evaporated and the residue was triturated with diethyl ether to yield after drying under vacuum 0.600 g (93%) of the title compound as white solid. MS (m/e): 343.3 (M+H)$^+$.

b) 6-(3-Piperidin-1-yl-propoxy)-quinoline-2-carboxylic acid 1:1 hydrochloride

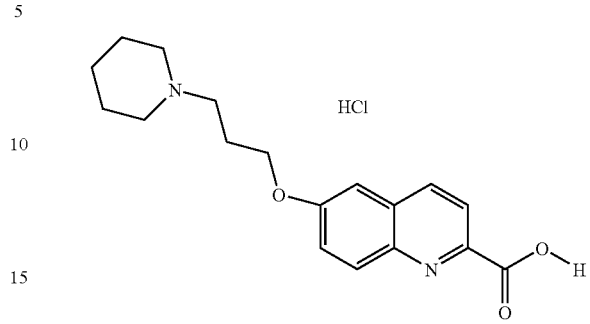

6-(3-Piperidin-1-yl-propoxy)-quinoline-2-carboxylic acid ethyl ester (0.6 g, 0.002 mol) was dissolved in dioxane (20 ml). HCl 37% (1.08 ml, 0.035 mol) was added and the mixture was stirred at 85° C. for 16 hours. Dioxane was evaporated and toluene (3×10 ml) was used to remove the remaining water by azeotropic distillation. After evaporation of the toluene the title compound was obtained as a yellow solid after drying under vacuum (0.592 g, 96% of theory). MS (m/e)=315.3(M+H)$^+$.

Intermediate 5

6-[2-(1-Methyl-pyrrolidin-2-yl)-ethoxy]-quinoline-2-carboxylic acid 1:1 hydrochloride a) 6-[2-(1-Methyl-pyrrolidin-2-yl)-ethoxy]-quinoline-2-carboxylic acid ethyl ester

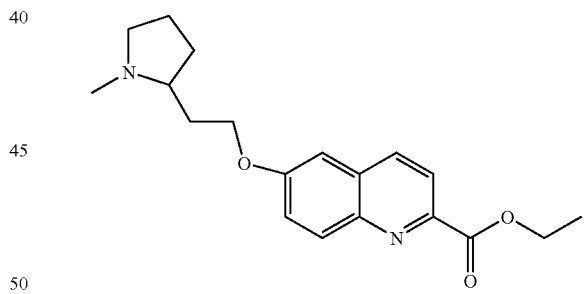

A mixture of 0.400 g (0.002 mol) of 6-hydroxy-quinoline-2-carboxylic acid ethyl ester, 0.966 g (0.004 mmol) of triphenylphospine (Fluka), 0.396 g (0.003 mmol) of 1-methyl-2-pyrrolidineethanol and 0.68 ml (0.004 mmol) di-tert.-butyl azadicarboxylate 40% in toluene in 40 ml THF was stirred for a prolonged period of time at 35° C. The mixture was filtered through a pad of silica and washed with 30 ml THF. The mixture was evaporated to dryness and purified on silica eluting with a gradient of DCM/MeOH/NH4OH from 97/3/0.5 to 90/10/0.5. The ]

product fractions were evaporated and the residue was triturated with diethyl ether to yield after drying under vacuum 0.317 g (53%) of the title compound as white solid. MS (m/e): 329.2 (M+H)$^+$.

b) 6-[2-(1-Methyl-pyrrolidin-2-yl)-ethoxy]-quinoline-2-carboxylic acid 1:1 hydrochloride

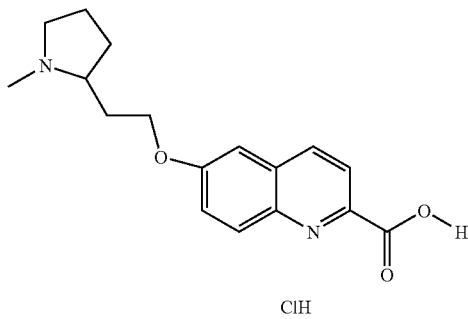

6-[2-(1-Methyl-pyrrolidin-2-yl)-ethoxy]-quinoline-2-carboxylic acid ethyl ester (0.310 g, 0.001 mol) was dissolved in dioxane (10 ml). HCl 37% (0.580 ml, 0.019 mol) was added and the mixture was stirred at 85° C. for 16 hours. Dioxane was evaporated and toluene (3×10 ml) was used to remove the remaining water by azeotropic distillation. After evaporation of the toluene the title compound was obtained as a yellow solid after drying under vacuum (0.395 g, 96% of theory). MS (m/e)=301.3 (M+H)$^+$.

Example 1

(2,5-Dihydro-pyrrol-1-yl)-[6-(1-isopropyl-piperidin-4-yloxy)-quinolin-2-yl]-methanone 6-(1-Isopropyl-piperidin-4-yloxy)-quinoline-2-carboxylic acid 1:1 hydrochloride (30 mg, 0.086 mmol, see intermediate 2) was dissolved in DMF (0.300 ml). 1,1'-Carbonyl-diimidazole (17 mg, 0.10 mmol) was added and the mixture was stirred for half an hour. 4-Methoxy-piperidine was added (6 mg, 0.014 mmol) and the mixture was stirred overnight. The mixture was diluted with 0.4 ml methanol and subjected to preparative HPLC purification on reversed phase material eluting with a gradient of acetonitrile/water/triethylamine. The product fractions were evaporated to dryness to yield 4.7 mg (14%) of the title compound as light brown solid. MS (m/e): 412.4 (MH$^+$, 100%).

According to the procedure described for the synthesis of example 1 further derivatives have been synthesized from 6-(1-isopropyl-piperidin-4-yloxy)-quinoline-2-carboxylic acid 1:1 hydrochloride and the respective amines. The results are shown in table 1 and comprise examples 2 to 26.

TABLE 1

| Ex. No | Systematic name | MW | Starting materials | MW found (M + H)$^+$ |
|---|---|---|---|---|
| 2 | (2,5-dihydro-pyrrol-1-yl)-[6-(1-isopropyl-piperidin-4-yloxy)-quinolin-2-yl]-methanone | 365.4 | 6-(1-isopropyl-piperidin-4-yloxy)-quinoline-2-carboxylic acid 1:1 hydrochloride and 5-dihydropyrrole (commercially available) | 366.4 |
| 3 | 6-(1-isopropyl-piperidin-4-yloxy)-quinoline-2-carboxylic acid ethyl-methyl-amide | 355.48 | 6-(1-isopropyl-piperidin-4-yloxy)-quinoline-2-carboxylic acid 1:1 hydrochloride and ethyl-methyl-amide (commercially available) | 356.4 |
| 4 | [6-(1-isopropyl-piperidin-4-yloxy)-quinolin-2-yl]-(2-methyl-pyrrolidin-1-yl)-methanone | 381.52 | 6-(1-isopropyl-piperidin-4-yloxy)-quinoline-2-carboxylic acid 1:1 hydrochloride and 2-methyl-pyrrolidine (commercially available) | 382.3 |
| 5 | 6-(1-isopropyl-piperidin-4-yloxy)-quinoline-2-carboxylic acid tert-butylamide | 369.51 | 6-(1-Isopropyl-piperidin-4-yloxy)-quinoline-2-carboxylic acid 1:1 hydrochloride and tert-butylamide (commercially available) | 370.3 |
| 6 | 6-(1-isopropyl-piperidin-4-yloxy)-quinoline-2-carboxylic acid cyclopropylmethyl-propyl-amide | 409.57 | 6-(1-isopropyl-piperidin-4-yloxy)-quinoline-2-carboxylic acid 1:1 hydrochloride and cyclopropylmethyl-propyl-amide (commercially available) | 410.5 |
| 7 | 6-(1-isopropyl-piperidin-4-yloxy)-quinolin-2-yl]-(2-methyl-piperidin-1-yl)-methanone | 395.55 | 6-(1-isopropyl-piperidin-4-yloxy)-quinoline-2-carboxylic acid 1:1 hydrochloride and 2-methyl-piperidine (commercially available) | 396.3 |
| 8 | (4-hydroxy-piperidin-1-yl)-[6-(1-isopropyl-piperidin-4-yloxy)-quinolin-2-yl]-methanone | 397.52 | 6-(1-isopropyl-piperidin-4-yloxy)-quinoline-2-carboxylic acid 1:1 hydrochloride and 4-hydroxy-piperidine (commercially available) | 398.4 |
| 9 | [6-(1-isopropyl-piperidin-4-yloxy)-quinolin-2-yl]-(3-methyl-piperidin-1-yl)-methanone | 395.55 | 6-(1-isopropyl-piperidin-4-yloxy)-quinoline-2-carboxylic acid 1:1 hydrochloride and 3-methyl-piperidine (commercially available) | 396.3 |
| 10 | (3,4-dihydro-1H-isoquinolin-2-yl)-[6-(3-piperidin-1-yl-propoxy)-naphthalen-2-yl]- | 369.51 | 6-(1-isopropyl-piperidin-4-yloxy)-quinoline-2-carboxylic acid 1:1 hydrochloride and isopropyl-methyl-amine | 370.4 |

TABLE 1-continued

| Ex. No | Systematic name | MW | Starting materials | MW found $(M + H)^+$ |
|---|---|---|---|---|
| | methanone 1:1 hydrochloride | | (commercially available) | |
| 11 | [6-(1-isopropyl-piperidin-4-yloxy)-quinolin-2-yl]-thiomorpholin-4-yl-methanone | 399.56 | 6-(1-isopropyl-piperidin-4-yloxy)-quinoline-2-carboxylic acid 1:1 hydrochloride and thiomorpholine (commercially available) | 400.4 |
| 12 | [6-(1-isopropyl-piperidin-4-yloxy)-quinolin-2-yl]-(2-trifluoromethyl-pyrrolidin-1-yl)-methanone | 435.49 | 6-(1-isopropyl-piperidin-4-yloxy)-quinoline-2-carboxylic acid 1:1 hydrochloride and 2-trifluoromethyl-pyrrolidine (commercially available) | 436.4 |
| 13 | 6-(1-isopropyl-piperidin-4-yloxy)-quinoline-2-carboxylic acid ethyl-(2-methoxy-ethyl)-amide | 399.53 | 6-(1-isopropyl-piperidin-4-yloxy)-quinoline-2-carboxylic acid 1:1 hydrochloride and ethyl-(2-methoxy-ethyl)-amine (commercially available) | 400.5 |
| 14 | azetidine-1-yl-[6-(1-isopropyl-piperidin-4-yloxy)-quinolin-2-yl]-methanone | 353.47 | 6-(1-isopropyl-piperidin-4-yloxy)-quinoline-2-carboxylic acid 1:1 hydrochloride and azetidine (commercially available) | 354.4 |
| 15 | (3,6-dihydro-2H-pyridin-1-yl)-[6-(1-isopropyl-piperidin-4-yloxy)-quinolin-2-yl]-methanone | 379.5 | 6-(1-isopropyl-piperidin-4-yloxy)-quinoline-2-carboxylic acid 1:1 hydrochloride and 1,2,3,6-tetrahydro-pyridine (commercially available) | 380.5 |
| 16 | 6-(1-isopropyl-piperidin-4-yloxy)-quinoline-2-carboxylic acid (3-fluoro-oxetan-3-ylmethyl)-amide | 411.55 | 6-(1-isopropyl-piperidin-4-yloxy)-quinoline-2-carboxylic acid 1:1 hydrochloride and (3-fluoro-oxetan-3-yl)-methylamine (commercially available) | 412.4 |
| 17 | 6-(1-isopropyl-piperidin-4-yloxy)-quinoline-2-carboxylic acid (1-methoxymethyl-cyclopropylmethyl)-amide | 411.55 | 6-(1-isopropyl-piperidin-4-yloxy)-quinoline-2-carboxylic acid 1:1 hydrochloride and (1-methoxymethyl-cyclopropyl)-methylamine (commercially available) | 412.4 |
| 18 | {6-(1-isopropyl-piperidin-4-yloxy)-quinoline-2-carboxylic acid [2-(tetrahydro-pyran-4-yl)-ethyl]-amide | 425.57 | 6-(1-isopropyl-piperidin-4-yloxy)-quinoline-2-carboxylic acid 1:1 hydrochloride and 2-(tetrahydro-pyran-4-yl)-ethylamine (commercially available) | 426.4 |
| 19 | [6-(1-isopropyl-piperidin-4-yloxy)-quinolin-2-yl]-morpholin-4-yl-methanone | 383.4 | 6-(1-isopropyl-piperidin-4-yloxy)-quinoline-2-carboxylic acid 1:1 hydrochloride and morpholine (commercially available) | 384.3 |
| 20 | 6-(1-isopropyl-piperidin-4-yloxy)-quinoline-2-carboxylic acid cyclohexyl-methyl-amide | 409.57 | 6-(1-isopropyl-piperidin-4-yloxy)-quinoline-2-carboxylic acid 1:1 hydrochloride and cyclohexyl-methyl-amide (commercially available) | 410.6 |
| 21 | (4,4-difluoro-piperidin-1-yl)-[6-(1-isopropyl-piperidin-4-yloxy)-quinolin-2-yl]-methanone | 417.497 | 6-(1-isopropyl-piperidin-4-yloxy)-quinoline-2-carboxylic acid 1:1 hydrochloride and 4,4-difluoro-piperidine (commercially available) | 418.3 |
| 22 | (3-hydroxy-pyrrolidin-1-yl)-[6-(1-isopropyl-piperidin-4-yloxy)-quinolin-2-yl]-methanone | 383.4 | 6-(1-isopropyl-piperidin-4-yloxy)-quinoline-2-carboxylic acid 1:1 hydrochloride and 3-hydroxy-pyrrolidine (commercially available) | 384.3 |
| 23 | [6-(1-isopropyl-piperidin-4-yloxy)-quinolin-2-yl]-pyrrolidin-1-yl-methanone | 367.49 | 6-(1-isopropyl-piperidin-4-yloxy)-quinoline-2-carboxylic acid 1:1 hydrochloride and pyrrolidine (commercially available) | 368.2 |
| 24 | (R)-1-[6-(1-isopropyl-piperidin-4-yloxy)-quinoline-2-carbonyl]-pyrrolidine-2-carbonitrile | 392.5 | 6-(1-isopropyl-piperidin-4-yloxy)-quinoline-2-carboxylic acid 1:1 hydrochloride and ((R)-pyrrolidine-2-carbonitrile (commercially available) | 393.3 |

TABLE 1-continued

| Ex. No | Systematic name | MW | Starting materials | MW found (M + H)+ |
|---|---|---|---|---|
| 25 | (1,1-dioxo--thiomorpholin-4-yl)-[6-(1-isopropyl-piperidin-4-yloxy)-quinolin-2-yl]-methanone | 431.5 | 6-(1-isopropyl-piperidin-4-yloxy)-quinoline-2-carboxylic acid 1:1 hydrochloride and thiomorpholine 1,1-dioxide | 432.4 |
| 26 | 6-(1-isopropyl-piperidin-4-yloxy)-quinoline-2-carboxylic acid dimethylamide | 341.5 | 6-(1-isopropyl-piperidin-4-yloxy)-quinoline-2-carboxylic acid 1:1 hydrochloride and dimethylamide (commercially available) | 342.2 |

Example 27

(2,5-Dihydro-pyrrol-1-yl)-[6-(1-isopropyl-pyrrolidin-3-yloxy)-quinolin-2-yl]-methanone According to the procedure described for the synthesis of example 1, (2,5-dihydro-pyrrol-1-yl)-[6-(1-isopropyl-pyrrolidin-3-yloxy)-quinolin-2-yl]-methanone was synthesized from 6-(1-isopropyl-pyrrolidin-3-yloxy)-quinoline-2-carboxylic acid 1:1 hydrochloride (intermediate 3) and 2,5-dihydropyrrole (commercially available). The title compound was yielded in 18% (5.7 mg) as off-white solid. MS (m/e): 352.5 (MH+, 100%).

Accordingly, further derivatives have been synthesized from 6-(1-isopropyl-pyrrolidin-3-yloxy)-quinoline-2-carboxylic acid 1:1 hydrochloride and the respective amines. The results are shown in table 2 and comprise examples 28 to 46.

TABLE 2

| Ex. No | Systematic name | MW | Starting materials | MW found (M + H)+ |
|---|---|---|---|---|
| 28 | ([6-(1-isopropyl-pyrrolidin-3-yloxy)-quinolin-2-yl]-(4-methoxy-piperidin-1-yl)-methanone | 397.52 | 6-(1-isopropyl-pyrrolidin-3-yloxy)-quinoline-2-carboxylic acid acid 1:1 hydrochloride and 4-methoxy-piperidine | 398.4 |
| 29 | 6-(1-isopropyl-pyrrolidin-3-yloxy)-quinoline-2-carboxylic acid ethyl-methyl-amide | 341.45 | 6-(1-isopropyl-pyrrolidin-3-yloxy)-quinoline-2-carboxylic acid acid 1:1 hydrochloride and ethyl-methyl-amide (commercially available) | 342.2 |
| 30 | ([6-(1-isopropyl-pyrrolidin-3-yloxy)-quinolin-2-yl]-(4-methyl-piperidin-1-yl)-methanone | 381.52 | 6-(1-isopropyl-pyrrolidin-3-yloxy)-quinoline-2-carboxylic acid acid 1:1 hydrochloride and 4-methyl-piperidine (commercially available) | 382.3 |
| 31 | [6-(1-isopropyl-pyrrolidin-3-yloxy)-quinolin-2-yl]-(2-methyl-pyrrolidin-1-yl)-methanone | 367.49 | 6-(1-isopropyl-pyrrolidin-3-yloxy)-quinoline-2-carboxylic acid acid 1:1 hydrochloride and 2-methyl-pyrrolidine (commercially available) | 368.3 |
| 32 | 6-(1-isopropyl-pyrrolidin-3-yloxy)-quinoline-2-carboxylic acid tert-butylamide | 355.48 | 6-(1-isopropyl-pyrrolidin-3-yloxy)-quinoline-2-carboxylic acid acid 1:1 hydrochloride and tert-butylamide (commercially available) | 356.4 |
| 33 | 6-(1-isopropyl-pyrrolidin-3-yloxy)-quinoline-2-carboxylic acid cyclopropylmethyl-propyl-amide | 395.55 | 6-(1-isopropyl-pyrrolidin-3-yloxy)-quinoline-2-carboxylic acid acid 1:1 hydrochloride and cyclopropylmethyl-propyl-amide (commercially available) | 396.3 |
| 34 | {[6-(1-isopropyl-pyrrolidin-3-yloxy)-quinolin-2-yl]-(2-methyl-piperidin-1-yl)-methanone | 381.52 | 6-(1-isopropyl-pyrrolidin-3-yloxy)-quinoline-2-carboxylic acid acid 1:1 hydrochloride and 2-methyl-piperidine (commercially available) | 382.3 |
| 35 | [6-(1-isopropyl-pyrrolidin-3-yloxy)-quinolin-2-yl]-(3-methyl-piperidin-1-yl)-methanone | 381.52 | 6-(1-isopropyl-pyrrolidin-3-yloxy)-quinoline-2-carboxylic acid acid 1:1 hydrochloride and 3-methyl-piperidine (commercially available) | 382.3 |

TABLE 2-continued

| Ex. No | Systematic name | MW | Starting materials | MW found (M + H)+ |
|---|---|---|---|---|
| 36 | 6-(1-isopropyl-pyrrolidin-3-yloxy)-quinoline-2-carboxylic acid isopropyl-methyl-amide | 355.48 | 6-(1-isopropyl-pyrrolidin-3-yloxy)-quinoline-2-carboxylic acid acid 1:1 hydrochloride and isopropyl-methyl-amine (commercially available) | 356.4 |
| 37 | [6-(1-isopropyl-pyrrolidin-3-yloxy)-quinolin-2-yl]-thiomorpholin-4-yl-methanone | 385.53 | 6-(1-isopropyl-pyrrolidin-3-yloxy)-quinoline-2-carboxylic acid acid 1:1 hydrochloride and thiomorpholine (commercially available) | 386.3 |
| 38 | [6-(1-isopropyl-pyrrolidin-3-yloxy)-quinolin-2-yl]-(2-trifluoromethyl-pyrrolidin-1-yl)-methanone | 421.46 | 6-(1-isopropyl-pyrrolidin-3-yloxy)-quinoline-2-carboxylic acid acid 1:1 hydrochloride and 2-trifluoromethyl-pyrrolidine (commercially available) | 422.3 |
| 39 | 6-(1-isopropyl-pyrrolidin-3-yloxy)-quinoline-2-carboxylic acid ethyl-(2-methoxy-ethyl)-amide | 385.51 | 6-(1-isopropyl-pyrrolidin-3-yloxy)-quinoline-2-carboxylic acid acid 1:1 hydrochloride and ethyl-(2-methoxy-ethyl)-amine (commercially available) | 386.4 |
| 40 | azetidin-1-yl-[6-(1-isopropyl-pyrrolidin-3-yloxy)-quinolin-2-yl]-methanone | 339.44 | 6-(1-isopropyl-pyrrolidin-3-yloxy)-quinoline-2-carboxylic acid acid 1:1 hydrochloride and azetidine (commercially available) | 340.3 |
| 41 | (3,6-dihydro-2H!-pyridin-1-yl)-[6-(1-isopropyl-pyrrolidin-3-yloxy)-quinolin-2-yl]-methanone | 365.48 | 6-(1-isopropyl-pyrrolidin-3-yloxy)-quinoline-2-carboxylic acid acid 1:1 hydrochloride and 1,2,3,6-tetrahydro-pyridine (commercially available) | 366.2 |
| 42 | 6-(1-isopropyl-pyrrolidin-3-yloxy)-quinoline-2-carboxylic acid (3-fluoro-oxetan-3-ylmethyl)-amide | 387.45 | 6-(1-isopropyl-pyrrolidin-3-yloxy)-quinoline-2-carboxylic acid acid 1:1 hydrochloride and (3-fluoro-oxetan-3-yl)-methylamine | 388.3 |
| 43 | 6-(1-isopropyl-pyrrolidin-3-yloxy)-quinoline-2-carboxylic acid (1-methoxymethyl-cyclopropylmethyl)-amide | 397.52 | 6-(1-isopropyl-pyrrolidin-3-yloxy)-quinoline-2-carboxylic acid acid 1:1 hydrochloride and (1-methoxymethyl-cyclopropyl)-methylamine | 398.4 |
| 44 | 6-(1-isopropyl-pyrrolidin-3-yloxy)-quinoline-2-carboxylic acid [2-(tetrahydro-pyran-4-yl)-ethyl]-amide | 411.55 | 6-(1-isopropyl-pyrrolidin-3-yloxy)-quinoline-2-carboxylic acid acid 1:1 hydrochloride and 2-(tetrahydro-pyran-4-yl)-ethylamine | 412.4 |
| 45 | (4,4-difluoro-piperidin-1-yl)-[6-(1-isopropyl-pyrrolidin-3-yloxy)-quinolin-2-yl]-methanone | 403.5 | 6-(1-isopropyl-pyrrolidin-3-yloxy)-quinoline-2-carboxylic acid acid 1:1 hydrochloride and 4,4-difluoro-piperidine (commercially available) | 404.4 |
| 46 | [6-(1-isopropyl-piperidin-4-yloxy)-quinolin-2-yl]-morpholin-4-yl-methanone | 369.4 | 6-(1-Isopropyl-pyrrolidin-3-yloxy)-quinoline-2-carboxylic acid acid 1:1 hydrochloride and morpholine (commercially available) | 370.3 |

Example 47

(4-Methoxy-piperidin-1-yl)-[6-(3-piperidin-1-yl-propoxy)-quinolin-2-yl]-methanone According to the procedure described for the synthesis of example 1, (4-methoxy-piperidin-1-yl)-[6-(3-piperidin-1-yl-propoxy)-quinolin-2-yl]-methanone was synthesized from 6-(3-piperidin-1-yl-propoxy)-quinoline-2-carboxylic acid 1:1 hydrochloride (intermediate 4) and 4-methoxy-piperidine (commercially available). The title compound was yielded in 22% (7.8 mg) as off-white solid. MS (m/e): 412.4 (MH+, 100%).

Accordingly, further derivatives have been synthesized from 6-(3-piperidin-1-yl-propoxy)-quinoline-2-carboxylic acid 1:1 hydrochloride and the respective amines. The results are shown in table 3 and comprise examples 48 to 66.

TABLE 3

| Ex. No | Systematic name | MW | Starting materials | MW found (M + H)+ |
|---|---|---|---|---|
| 48 | (4-methyl-piperidin-1-yl)-[6-(3-piperidin-1-yl-propoxy)-quinolin-2-yl]-methanone | 395.55 | 6-(3-piperidin-1-yl-propoxy)-quinoline-2-carboxylic acid 1:1 hydrochloride and 4-methyl-piperidine (commercially available) | 396.3 |
| 49 | morpholin-4-yl-[6-(3-piperidin-1-yl-propoxy)-quinolin-2-yl]-methanone | 383.49 | 6-(3-piperidin-1-yl-propoxy)-quinoline-2-carboxylic acid 1:1 hydrochloride and morpholine (commercially available) | 384.3 |
| 50 | (2-methyl-pyrrolidin-1-yl)-[6-(3-piperidin-1-yl-propoxy)-quinolin-2-yl]-methanone | 381.52 | 6-(3-piperidin-1-yl-propoxy)-quinoline-2-carboxilic acid 1:1 hydrochloride and 2-methyl-pyrrolidine (commercially available) | 382.4 |
| 51 | 6-(3-piperidin-1-yl-propoxy)-quinoline-2-carboxylic acid cyclopropylmethyl-propyl-amide | 409.57 | 6-(3-piperidin-1-yl-propoxy)-quinoline-2-carboxylic acid 1:1 hydrochloride and cyclopropylmethyl-propyl-amide (commercially available) | 410.4 |
| 52 | [6-(3-piperidin-1-yl-propoxy)-quinolin-2-yl]-(2-trifluoromethyl-pyrrolidin-1-yl)-methanone | 435.49 | 6-(3-piperidin-1-yl-propoxy)-quinoline-2-carboxylic acid 1:1 hydrochloride and 2-trifluoromethyl-pyrrolidine (commercially available) | 436.3 |
| 53 | (2,5-dihydro-pyrrol-1-yl)-[6-(3-piperidin-1-yl-propoxy)-quinolin-2-yl]-methanone | 365.48 | 6-(3-piperidin-1-yl-propoxy)-quinoline-2-carboxylic acid 1:1 hydrochloride and 2,5-dihydropyrrole (commercially available) | 366.3 |
| 54 | 6-(3-piperidin-1-yl-propoxy)-quinoline-2-carboxylic acid ethyl-(2-methoxy-ethyl)-amide | 399.53 | 6-(3-piperidin-1-yl-propoxy)-quinoline-2-carboxylic acid 1:1 hydrochloride and ethyl-(2-methoxy-ethyl)-amine (commercially available) | 400.3 |
| 55 | azetidin-1-yl-[6-(3-piperidin-1-yl-propoxy)-quinolin-2-yl]-methanone | 353.47 | 6-(3-piperidin-1-yl-propoxy)-quinoline-2-carboxylic acid 1:1 hydrochloride and azetidine (commercially available) | 354.3 |
| 56 | (3,6-dihydro-2H-pyridin-1-yl)-[6-(3-piperidin-1-yl-propoxy)-quinolin-2-yl]-methanone | 379.5 | 6-(3-piperidin-1-yl-propoxy)-quinoline-2-carboxylic acid 1:1 hydrochloride and 1,2,3,6-tetrahydro-pyridine (commercially available) | 380.4 |
| 57 | (4,4-difluoro-piperidin-1-yl)-[6-(3-piperidin-1-yl-propoxy)-quinolin-2-yl]-methanone | 417.5 | 6-(3-piperidin-1-yl-propoxy)-quinoline-2-carboxylic acid 1:1 hydrochloride and 4,4-difluoro-piperidine (commercially available) | 418.4 |
| 58 | 6-(3-piperidin-1-yl-propoxy)-quinoline-2-carboxylic acid cyclohexyl-methyl-amide | 409.57 | 6-(3-piperidin-1-yl-propoxy)-quinoline-2-carboxylic acid 1:1 hydrochloride and cyclohexyl-methyl-amide (commercially available) | 410.4 |
| 59 | 6-(3-piperidin-1-yl-propoxy)-quinoline-2-carboxylic acid (1-methoxymethyl-cyclopropylmethyl)-amide | 411.55 | 6-(3-piperidin-1-yl-propoxy)-quinoline-2-carboxylic acid 1:1 hydrochloride and (1-methoxymethyl-cyclopropyl)-methylamine (commercially available) | 412.4 |
| 60 | 6-(3-piperidin-1-yl-propoxy)-quinoline-2-carboxylic acid (3-fluoro-oxetan-3-ylmethyl)-amide | 401.48 | 6-(3-piperidin-1-yl-propoxy)-quinoline-2-carboxylic acid 1:1 hydrochloride and (3-fluoro-oxetan-3-yl)-methylamine (commercially available) | 402.4 |
| 61 | 6-(3-piperidin-1-yl-propoxy)-quinoline-2-carboxylic acid [2-(tetrahydro-pyran-4-yl)-ethyl]-amide | 425.57 | 6-(3-piperidin-1-yl-propoxy)-quinoline-2-carboxylic acid 1:1 hydrochloride and 2-(tetrahydro-pyran-4-yl)-ethylamine (commercially available) | 426.3 |

TABLE 3-continued

| Ex. No | Systematic name | MW | Starting materials | MW found (M + H)+ |
|---|---|---|---|---|
| 62 | 6-(3-piperidin-1-yl-propoxy)-quinoline-2-carboxylic acid (tetrahydro-pyran-4-yl)-amide | 397.52 | 6-(3-piperidin-1-yl-propoxy)-quinoline-2-carboxylic acid 1:1 hydrochloride and 4-amino-tetrahydropyran (commercially available) | 398.3 |
| 63 | (2-methyl-piperidin-1-yl)-[6-(3-piperidin-1-yl-propoxy)-quinolin-2-yl]-methanone | 395.55 | 6-(3-piperidin-1-yl-propoxy)-quinoline-2-carboxylic acid 1:1 hydrochloride and 2-methyl-piperidine (commercially available) | 396.3 |
| 64 | [6-(3-piperidin-1-yl-propoxy)-quinolin-2-yl]-pyrrolidin-1-yl-methanone | 367.49 | 6-(3-piperidin-1-yl-propoxy)-quinoline-2-carboxylic acid 1:1 hydrochloride and pyrrolidine (commercially available) | 368.2 |
| 65 | (R)-1-[6-(3-piperidin-1-yl-propoxy)-quinoline-2-carbonyl]-pyrrolidine-2-carbonitrile | 392.5 | 6-(3-piperidin-1-yl-propoxy)-quinoline-2-carboxylic acid 1:1 hydrochloride and ((R)-pyrrolidine-2-carbonitrile (commercially available) | 393.3 |
| 66 | (1,1-dioxo--thiomorpholin-4-yl)-[6-(3-piperidin-1-yl-propoxy)-quinolin-2-yl]-methanone | 431.55 | 6-(3-piperidin-1-yl-propoxy)-quinoline-2-carboxylic acid 1:1 hydrochloride and thiomorpholine 1,1-dioxide | 432.4 |

Example 67

(4-Methyl-piperidin-1-yl)-{6-[2-(1-methyl-pyrrolidin-2-yl)-ethoxy]-quinolin-2-yl}-methanone According to the procedure described for the synthesis of example 1, (4-methyl-piperidin-1-yl)-{6-[2-(1-methyl-pyrrolidin-2-yl)-ethoxy]-quinolin-2-yl}-methanone was synthesized from 6-[2-(1-methyl-pyrrolidin-2-yl)-ethoxy]-quinoline-2-carboxylic acid 1:1 hydrochloride (intermediate 5) and 4-methyl-piperidine (commercially available). The title compound was yielded in 13% (4.2 mg) as white solid. MS (m/e): 382.4 (MH+, 100%).

According to the procedure described for the synthesis of example 67 further derivatives have been synthesized from 6-[2-(1-methyl-pyrrolidin-2-yl)-ethoxy]-quinoline-2-carboxylic acid 1:1 hydrochloride and the respective amines. The results are shown in table 4 and comprise examples 68 to 76.

TABLE 4

| Ex. No | Systematic name | MW | Starting materials | MW found (M + H)+ |
|---|---|---|---|---|
| 68 | {6-[2-(1-Methyl-pyrrolidin-2-yl)-ethoxy]-quinolin-2-yl}-pyrrolidin-1-yl-methanone | 353.47 | 6-[2-(1-methyl-pyrrolidin-2-yl)-ethoxy]-quinoline-2-carboxylic acid 1:1 hydrochloride and pyrrolidine (commercially available) | 354.3 |
| 69 | (R)-1-{6-[2-(1-methyl-pyrrolidin-2-yl)-ethoxy]-quinoline-2-carbonyl}-pyrrolidine-2-carbonitrile | 378.48 | 6-[2-(1-methyl-pyrrolidin-2-yl)-ethoxy]-quinoline-2-carboxylic acid 1:1 hydrochloride and ((R)-pyrrolidine-2-carbonitrile (commercially available) | 379.4 |
| 70 | (1,1-dioxo-thiomorpholin-4-yl)-{6-[2-(1-methyl-pyrrolidin-2-yl)-ethoxy]-quinolin-2-yl}-methanone | 417.53 | 6-[2-(1-methyl-pyrrolidin-2-yl)-ethoxy]-quinoline-2-carboxylic acid 1:1 hydrochloride and thiomorpholine 1,1-dioxide | 418.4 |
| 71 | (4-methoxy-piperidin-1-yl)-{6-[2-(1-methyl-pyrrolidin-2-yl)-ethoxy]-quinolin-2-yl}-methanone | 397.52 | 6-[2-(1-methyl-pyrrolidin-2-yl)-ethoxy]-quinoline-2-carboxylic acid 1:1 hydrochloride and 4-methoxy-piperidine (commercially available) | 398.3 |
| 72 | {6-[2-(1-methyl-pyrrolidin-2-yl)-ethoxy]-quinolin-2-yl}-morpholin-4-yl-methanone | 369.46 | 6-[2-(1-methyl-pyrrolidin-2-yl)-ethoxy]-quinoline-2-carboxylic acid 1:1 hydrochloride and morpholine (commercially available) | 370.3 |

TABLE 4-continued

| Ex. No | Systematic name | MW | Starting materials | MW found (M + H)+ |
|---|---|---|---|---|
| 73 | azetidin-1-yl-{6-[2-(1-methyl-pyrrolidin-2-yl)-ethoxy]-quinolin-2-yl}-methanone | 339.44 | 6-[2-(1-methyl-pyrrolidin-2-yl)-ethoxy]-quinoline-2-carboxylic acid 1:1 hydrochloride and azetidine (commercially available) | 340.3 |
| 74 | 6-[2-(1-methyl-pyrrolidin-2-yl)-ethoxy]-quinoline-2-carboxylic acid [2-(tetrahydro-pyran-4-yl)-ethyl]-amide | 411.55 | 6-[2-(1-methyl-pyrrolidin-2-yl)-ethoxy]-quinoline-2-carboxylic acid 1:1 hydrochloride and 2-(tetrahydro-pyran-4-yl)-ethylamine (commercially available) | 412.4 |
| 75 | 6-[2-(1-methyl-pyrrolidin-2-yl)-ethoxy]-quinoline-2-carboxylic acid (3-fluoro-oxetan-3-ylmethyl)-amide | 387.45 | 6-[2-(1-methyl-pyrrolidin-2-yl)-ethoxy]-quinoline-2-carboxylic acid 1:1 hydrochloride and (3-fluoro-oxetan-3-yl)-methylamine (commercially available) | 388.3 |
| 76 | (2-methyl-pyrrolidin-1-yl)-{6-[2-(1-methyl-pyrrolidin-2-yl)-ethoxy]-quinolin-2-yl}-methanone | 367.49 | 6-[2-(1-methyl-pyrrolidin-2-yl)-ethoxy]-quinoline-2-carboxylic acid 1:1 hydrochloride and 2-methyl-pyrrolidine (commercially available) | 368.2 |

Example 77

(S)-1-[6-(1-Isopropyl-piperidin-4-yloxy)-quinoline-2-carbonyl]-pyrrolidine-2-carbonitrile According to the procedure described for the synthesis of example 1, (S)-1-[6-(1-isopropyl-piperidin-4-yloxy)-quinoline-2-carbonyl]-pyrrolidine-2-carbonitrile was synthesized from 6-(1-isopropyl-piperidin-4-yloxy)-quinoline-2-carboxylic acid 1:1 hydrochloride, (S)-cyanopyrrolidine (commercially available) and O-(benzotriazol-1-yl)-N,N,N',N'-tetramethyluronium tetrafluoroborate instead of 1,1'-carbonyl-diimidazole. The title compound was yielded in 45% (50 mg) as colorless foam. MS (m/e): 392.9 (M).

Example 78

[6-(1-Isopropyl-piperidin-4-yloxy)-quinolin-2-yl]-(4-methyl-piperidin-1-yl)-methanone According to the procedure described for the synthesis of example 1, [6-(1-isopropyl-piperidin-4-yloxy)-quinolin-2-yl]-(4-methyl-piperidin-1-yl)-methanone was synthesized from 6-(1-isopropyl-piperidin-4-yloxy)-quinoline-2-carboxylic acid 1:1 hydrochloride, 4-methylpiperidine (commercially available) and 1,1-carbonyl-diimidazole. MS (m/e): 396.6 (M+H).

Example 79

(4-Hydroxymethyl-piperidin-1-yl)-[6-(1-isopropyl-piperidin-4-yloxy)-quinolin-2-yl]-methanone According to the procedure described for the synthesis of example 1, (4-hydroxymethyl-piperidin-1-yl)-[6-(1-isopropyl-piperidin-4-yloxy)-quinolin-2-yl]-methanone was synthesized from 6-(1-isopropyl-piperidin-4-yloxy)-quinoline-2-carboxylic acid 1:1 hydrochloride, 4-hydroxymethyl piperidine (commercially available) and 1,1'-carbonyl-diimidazole. MS (m/e): 412.5 (M+H).

Example 80

6-(1-Isopropyl-piperidin-4-yloxy)-quinoline-2-carboxylic acid isobutyl-amide

According to the procedure described for the synthesis of example 1, (6-(1-isopropyl-piperidin-4-yloxy)-quinoline-2-carboxylic acid isobutyl-amide was synthesized from 6-(1-isopropyl-piperidin-4-yloxy)-quinoline-2-carboxylic acid 1:1 hydrochloride, isobutylamine (commercially available) and 1,1'-carbonyl-diimidazole. MS (m/e): 370.6 (M+H).

Example 81

6-(1-Isopropyl-pyrrolidin-3-yloxy)-quinoline-2-carboxylic acid cyclohexyl-methyl-amide According to the procedure described for the synthesis of example 27, 6-(1-isopropyl-pyrrolidin-3-yloxy)-quinoline-2-carboxylic acid cyclohexyl-methyl-amide was synthesized from 6-(1-isopropyl-pyrrolidin-3-yloxy)-quinoline-2-carboxylic acid 1:1 hydrochloride (intermediate 3), N-methyl-cyclohexylamine (commercially available) and 1,1'-carbonyl-diimidazole. MS (m/e): 396.4 (M+H).

Example 82

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |

-continued

| Ingredients | Per tablet | |
|---|---|---|
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example 83

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 84

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 85

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 86

Sachets containing the following ingredients can be manufactured in a conventional manner:

| | |
|---|---|
| Compound of formula (I) | 50.0 mg |
| Lactose, fine powder | 1015.0 mg |
| microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Example 87

The following test was carried out in order to determine the activity of the compounds of formula (I).

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)(X-Methylhistamine dihydrobromide (500 nM final concentration). The incubation was carried out at room temperature (in deep-well plates shaking for three hours). The final volume in each well was 250 pt. The incubation was followed by rapid filtration on GF/B filters (pre-soaked with 100 W of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM MgCl$_2$×6H$_2$O pH 7.4. Washing Buffer: 50 mM Tris-HCl pH 7.4 and 5 mM MgCl$_2$×6H$_2$O and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine IC$_{50}$ in a serial dilution experiment. Ki's were calculated from IC$_{50}$ based on Cheng-Prusoff equation (Cheng, Y, Prusoff, W H (1973) Biochem Pharmacol 22, 3099-3108).

The compounds of the present invention exhibit K$_i$ values within the range of about 1 nM to about 1000 nM, preferably of about 1 nM to about 100 nM, and more preferably of about 1 nM to about 30 nM. The following table shows measured values for some selected compounds of the present invention.

The following table shows measured values for some selected compounds of the present invention.

| Compound | K$_i$ (nM) |
| --- | --- |
| Example 2 | 200 |
| Example 14 | 78 |
| Example 64 | 450 |

It is to be understood that the invention is not limited to the particular embodiments of the invention described above, as variations of the particular embodiments may be made and still fall within the scope of the appended claims.

What is claimed is:

1. A compound of the formula 1, wherein:
R$^1$ is selected from the group consisting of hydrogen, lower alkyl, lower alkenyl,
  cycloalkyl, lower cycloalkylalkyl, wherein the cycloalkyl ring may be unsubstituted or substituted by one or two groups selected from the group consisting of lower alkyl, lower hydroxyalkyl and lower alkoxyalkyl,
  lower hydroxyalkyl,
  lower alkoxyalkyl, and
  lower heterocyclylalkyl, wherein the heterocyclyl ring may be unsubstituted or substituted by one or two groups selected from lower alkyl and halogen;
R$^2$ is selected from the group consisting of hydrogen, lower alkyl, lower alkenyl,
  cycloalkyl, lower cycloalkylalkyl, wherein the cycloalkyl ring may be unsubstituted or substituted by one or two groups selected from the group consisting of lower alkyl, lower hydroxyalkyl and lower alkoxyalkyl,
  lower hydroxyalkyl,
  lower alkoxyalkyl, and
  lower heterocyclylalkyl, wherein the heterocyclyl ring may be unsubstituted or substituted by one or two groups selected from lower alkyl and halogen; or
R$^1$ and R$^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated or partly unsaturated heterocyclic ring being unsubstituted or substituted by one, two or three groups independently selected from the group consisting of lower alkyl, halogen, halogenalkyl, cyano, hydroxy, hydroxyalkyl, lower alkoxy, oxo, phenyl, benzyl, pyridyl and carbamoyl;

A is selected from

A1

A2 or

A3 wherein
m is 0, 1 or 2;
R$^3$ is lower alkyl;
n is 0, 1 or 2;
R$^4$ is lower alkyl;
p is 0, 1 or 2;
q is 0, 1 or 2;
R$^5$ is hydrogen or lower alkyl;

and pharmaceutically acceptable salts thereof.

2. The compound according to claim 1, wherein R$^1$ is selected from the group consisting of hydrogen, lower alkyl, lower alkenyl,
  cycloalkyl or lower cycloalkylalkyl, wherein the cycloalkyl ring may be unsubstituted or substituted by one or two groups selected from lower alkyl, lower hydroxyalkyl and lower alkoxyalkyl,
  lower hydroxyalkyl, lower alkoxyalkyl, and
  lower heterocyclylalkyl, wherein the heterocyclyl ring may be unsubstituted or substituted with one or two groups selected from lower alkyl and halogen, and
R$^2$ is hydrogen or lower alkyl.

3. The compound according to claim 1, wherein R$^1$ is selected from the group consisting of lower alkyl,
  cycloalkyl or lower cycloalkylalkyl, wherein the cycloalkyl ring may be unsubstituted or substituted by lower alkoxyalkyl,
  lower alkoxyalkyl, and
  lower heterocyclylalkyl wherein the heterocyclyl ring may be unsubstituted or substituted with one or two groups selected from lower alkyl or halogen,
  and R$^2$ is hydrogen or lower alkyl.

4. The compound according to claim 3, wherein R$^1$ and R$^2$ are lower alkyl.

5. The compound according to claim 1, wherein R$^1$ and R$^2$ together with the nitrogen atom to which they are attached form a 4-, 5-, 6- or 7-membered saturated or partly unsaturated heterocyclic ring optionally containing a further heteroatom selected from nitrogen, oxygen or sulfur, said heterocyclic ring being unsubstituted or substituted by one, two or three groups independently selected from lower alkyl, halogen, halogenalkyl, cyano, hydroxy, lower alkoxy, oxo, phenyl, benzyl, pyridyl and carbamoyl.

6. The compound according to claim 1, wherein $R^1$ and $R^2$ together with the nitrogen atom to which they are attached form a 4-, 5-, or 6- or 7-membered saturated or partly unsaturated heterocyclic ring optionally containing a further heteroatom selected from nitrogen, oxygen or sulfur, said heterocyclic ring being unsubstituted or substituted by one, two or three groups independently selected from lower alkyl, halogen, halogenalkyl, cyano, hydroxy, lower alkoxy, and oxo.

7. The compound according to claim 1, wherein $R^1$ and $R^2$ together with the nitrogen atom to which they are attached form a heterocyclic ring selected from the group consisting of morpholine, piperidine, 2,5-dihydropyrrole, pyrrolidine, azepane, piperazine, azetidine, thiomorpholine and 3,6-dihydro-2H-pyridine, said heterocyclic ring being unsubstituted or substituted by one, two or three groups independently selected from lower alkyl, halogen, halogenalkyl, cyano, hydroxy, lower alkoxy, and oxo.

8. The compound according to claim 1, wherein $R^1$ and $R^2$ together with the nitrogen atom to which they are attached form a heterocyclic ring selected from morpholinyl, thiomorpholinyl, 1,1-dioxothiomorpholinyl, 3,6-dihydro-2H-pyridinyl, piperidinyl, 2-methylpiperidinyl, 3-methylpiperidinyl, 4-hydroxypiperidinyl, 4, 4-difluoropiperidinyl, 2,5-dihydropyrrolyl, 4-methylpiperidinyl, pyrrolidinyl, 2-methylpyrrolidinyl, 2-trifluoromethylpyrrolidinyl, 2-cyanopyrrolidinyl, 3-hydroxypyrrolidinyl and azetidinyl.

9. The compound according to claim 1, wherein A signifies

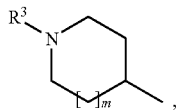

A1 wherein m is 0, 1 or 2, and $R^3$ is lower alkyl.

10. The compound according to claim 9, wherein m is 0.
11. The compound according to claim 9, wherein m is 1.
12. The compound according to claim 1, wherein A signifies

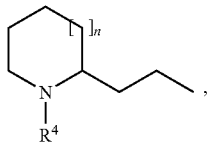

A2 wherein n is 0, 1 or 2; and $R^4$ is lower alkyl.

13. The compound according to claim 12, wherein n is 0.
14. The compound according to claim 1, wherein A signifies

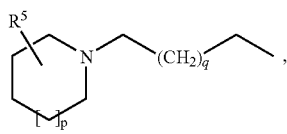

A3 wherein p is 0, 1 or 2, q is 0, 1 or 2, and $R^5$ is hydrogen or lower alkyl.

15. The compound according to claim 14, wherein p is 1.
16. The compound according to claim 14, wherein $R^5$ is hydrogen.

17. The compound according to claim 1, selected from the group consisting of
[6-(1-isopropyl-piperidin-4-yloxy)-quinolin-2-yl]-(4-methoxy-piperidin-1-yl)-methanone,
(2,5-dihydro-pyrrol-1-yl)-[6-(1-isopropyl-piperidin-4-yloxy)-quinolin-2-yl]-methanone,
6-(1-isopropyl-piperidin-4-yloxy)-quinoline-2-carboxylic acid ethyl-methyl-amide,
[6-(1-isopropyl-piperidin-4-yloxy)-quinolin-2-yl]-(2-methyl-pyrrolidin-1-yl)-methanone,
6-(1-isopropyl-piperidin-4-yloxy)-quinoline-2-carboxylic acid tert-butylamide,
6-(1-isopropyl-piperidin-4-yloxy)-quinoline-2-carboxylic acid cyclopropylmethyl-propyl-amide,
6-(1-isopropyl-piperidin-4-yloxy)-quinolin-2-yl]-(2-methyl-piperidin-1-yl)-methanone,
(4-hydroxy-piperidin-1-yl)-[6-(1-isopropyl-piperidin-4-yloxy)-quinolin-2-yl]-methanone,
[6-(1-isopropyl-piperidin-4-yloxy)-quinolin-2-yl]-(3-methyl-piperidin-1-yl)-methanone,
(3,4-dihydro-1H-isoquinolin-2-yl)-[6-(3-piperidin-1-yl-propoxy)-naphthalen-2-yl]-methanone 1:1 hydrochloride,
[6-(1-isopropyl-piperidin-4-yloxy)-quinolin-2-yl]-thiomorpholin-4-yl-methanone,
[6-(1-isopropyl-piperidin-4-yloxy)-quinolin-2-yl]-(2-trifluoromethyl-pyrrolidin-1-yl)-methanone,
6-(1-isopropyl-piperidin-4-yloxy)-quinoline-2-carboxylic acid ethyl-(2-methoxy-ethyl)-amide,
azetidin-1-yl-[6-(1-isopropyl-piperidin-4-yloxy)-quinolin-2-yl]-methanone,
(3,6-dihydro-2H-pyridin-1-yl)-[6-(1-isopropyl-piperidin-4-yloxy)-quinolin-2-yl]-methanone,
6-(1-isopropyl-piperidin-4-yloxy)-quinoline-2-carboxylic acid (3-fluoro-oxetan-3-ylmethyl)-amide,
6-(1-isopropyl-piperidin-4-yloxy)-quinoline-2-carboxylic acid (1-methoxymethyl-cyclopropylmethyl)-amide,
{6-(1-isopropyl-piperidin-4-yloxy)-quinoline-2-carboxylic acid [2-(tetrahydro-pyran-4-yl)-ethyl]-amide,
[6-(1-isopropyl-piperidin-4-yloxy)-quinolin-2-yl]-morpholin-4-yl-methanone,
6-(1-isopropyl-piperidin-4-yloxy)-quinoline-2-carboxylic acid cyclohexyl-methyl-amide,
(4,4-difluoro-piperidin-1-yl)-[6-(1-isopropyl-piperidin-4-yloxy)-quinolin-2-yl]-methanone,
(3-hydroxy-pyrrolidin-1-yl)-[6-(1-isopropyl-piperidin-4-yloxy)-quinolin-2-yl]-methanone,
[6-(1-isopropyl-piperidin-4-yloxy)-quinolin-2-yl]-pyrrolidin-1-yl-methanone,
(R)-1-[6-(1-isopropyl-piperidin-4-yloxy)-quinoline-2-carbonyl]-pyrrolidine-2-carbonitrile,
(1,1-dioxo-thiomorpholin-4-yl)-[6-(1-isopropyl-piperidin-4-yloxy)-quinolin-2-yl]-methanone,
6-(1-isopropyl-piperidin-4-yloxy)-quinoline-2-carboxylic acid dimethylamide,
(2,5-dihydro-pyrrol-1-yl)-[6-(1-isopropyl-pyrrolidin-3-yloxy)-quinolin-2-yl]-methanone,
([6-(1-isopropyl-pyrrolidin-3-yloxy)-quinolin-2-yl]-(4-methoxy-piperidin-1-yl)-methanone,
6-(1-isopropyl-pyrrolidin-3-yloxy)-quinoline-2-carboxylic acid ethyl-methyl-amide,
([6-(1-isopropyl-pyrrolidin-3-yloxy)-quinolin-2-yl]-(4-methyl-piperidin-1-yl)-methanone,
[6-(1-isopropyl-pyrrolidin-3-yloxy)-quinolin-2-yl]-(2-methyl-pyrrolidin-1-yl)-methanone,
6-(1-isopropyl-pyrrolidin-3-yloxy)-quinoline-2-carboxylic acid tert-butylamide,
6-(1-isopropyl-pyrrolidin-3-yloxy)-quinoline-2-carboxylic acid cyclopropylmethyl-propyl-amide, {[6-(1-isopropyl-pyrrolidin-3-yloxy)-quinolin-2-yl]-(2-methyl-piperidin-1-yl)-methanone,
[6-(1-isopropyl-pyrrolidin-3-yloxy)-quinolin-2-yl]-(3-methyl-piperidin-1-yl)-methanone,
6-(1-isopropyl-pyrrolidin-3-yloxy)-quinoline-2-carboxylic acid isopropyl-methyl-amide,
[6-(1-isopropyl-pyrrolidin-3-yloxy)-quinolin-2-yl]-thiomorpholin-4-yl-methanone,
[6-(1-isopropyl-pyrrolidin-3-yloxy)-quinolin-2-yl]-(2-trifluoromethyl-pyrrolidin-1-yl)-methanone,
6-(1-isopropyl-pyrrolidin-3-yloxy)-quinoline-2-carboxylic acid ethyl-(2-methoxy-ethyl)-amide,
azetidin-1-yl-[6-(1-isopropyl-pyrrolidin-3-yloxy)-quinolin-2-yl]-methanone,
(3,6-dihydro-2H!-pyridin-1-yl)-[6-(1-isopropyl-pyrrolidin-3-yloxy)-quinolin-2-yl]-methanone,
6-(1-isopropyl-pyrrolidin-3-yloxy)-quinoline-2-carboxylic acid (3-fluoro-oxetan-3-ylmethyl)-amide,
6-(1-isopropyl-pyrrolidin-3-yloxy)-quinoline-2-carboxylic acid (1-methoxymethyl-cyclopropylmethyl)-amide,
6-(1-isopropyl-pyrrolidin-3-yloxy)-quinoline-2-carboxylic acid [2-(tetrahydro-pyran-4-yl)-ethyl]-amide,
(4,4-difluoro-piperidin-1-yl)-[6-(1-isopropyl-pyrrolidin-3-yloxy)-quinolin-2-yl]-methanone,
[6-(1-isopropyl-piperidin-4-yloxy)-quinolin-2-yl]-morpholin-4-yl-methanone,
(4-methoxy-piperidin-1-yl)-[6-(3-piperidin-1-yl-propoxy)-quinolin-2-yl]-methanone,
(4-methyl-piperidin-1-yl)-[6-(3-piperidin-1-yl-propoxy)-quinolin-2-yl]-methanone,
morpholin-4-yl-[6-(3-piperidin-1-yl-propoxy)-quinolin-2-yl]-methanone,
(2-methyl-pyrrolidin-1-yl)-[6-(3-piperidin-1-yl-propoxy)-quinolin-2-yl]-methanone,
6-(3-piperidin-1-yl-propoxy)-quinoline-2-carboxylic acid cyclopropylmethyl-propyl-amide,
[6-(3-piperidin-1-yl-propoxy)-quinolin-2-yl]-(2-trifluoromethyl-pyrrolidin-1-yl)-methanone,
(2,5-dihydro-pyrrol-1-yl)-[6-(3-piperidin-1-yl-propoxy)-quinolin-2-yl]-methanone,
6-(3-piperidin-1-yl-propoxy)-quinoline-2-carboxylic acid ethyl-(2-methoxy-ethyl)-amide,
azetidin-1-yl-[6-(3-piperidin-1-yl-propoxy)-quinolin-2-yl]-methanone,
(3,6-dihydro-2H!-pyridin-1-yl)-[6-(3-piperidin-1-yl-propoxy)-quinolin-2-yl]-methanone,
(4,4-difluoro-piperidin-1-yl)-[6-(3-piperidin-1-yl-propoxy)-quinolin-2-yl]-methanone,
6-(3-piperidin-1-yl-propoxy)-quinoline-2-carboxylic acid cyclohexyl-methyl-amide,
6-(3-piperidin-1-yl-propoxy)-quinoline-2-carboxylic acid (1-methoxymethyl-cyclopropylmethyl)-amide,
6-(3-piperidin-1-yl-propoxy)-quinoline-2-carboxylic acid (3-fluoro-oxetan-3-ylmethyl)-amide,
6-(3-piperidin-1-yl-propoxy)-quinoline-2-carboxylic acid [2-(tetrahydro-pyran-4-yl)-ethyl]-amide,
6-(3-piperidin-1-yl-propoxy)-quinoline-2-carboxylic acid (tetrahydro-pyran-4-yl)-amide,
(2-methyl-piperidin-1-yl)-[6-(3-piperidin-1-yl-propoxy)-quinolin-2-yl]-methanone,
[6-(3-piperidin-1-yl-propoxy)-quinolin-2-yl]-pyrrolidin-1-yl-methanone,
(R)-1-[6-(3-piperidin-1-yl-propoxy)-quinoline-2-carbonyl]-pyrrolidine-2-carbonitrile,
(1,1-dioxo-thiomorpholin-4-yl)-[6-(3-piperidin-1-yl-propoxy)-quinolin-2-yl]-methanone,
(4-methyl-piperidin-1-yl)-{6-[2-(1-methyl-pyrrolidin-2-yl)-ethoxy]-quinolin-2-yl}-methanone,
{6-[2-(1-methyl-pyrrolidin-2-yl)-ethoxy]-quinolin-2-yl}-pyrrolidin-1-yl-methanone,
(R)-1-{6-[2-(1-methyl-pyrrolidin-2-yl)-ethoxy]-quinoline-2-carbonyl}-pyrrolidine-2-carbonitrile,
(1,1-dioxo-thiomorpholin-4-yl)-{6-[2-(1-methyl-pyrrolidin-2-yl)-ethoxy]-quinolin-2-yl}-methanone,
(4-methoxy-piperidin-1-yl)-{6-[2-(1-methyl-pyrrolidin-2-yl)-ethoxy]-quinolin-2-yl}-methanone,
{6-[2-(1-methyl-pyrrolidin-2-yl)-ethoxy]-quinolin-2-yl}-morpholin-4-yl-methanone,
azetidin-1-yl-{6-[2-(1-methyl-pyrrolidin-2-yl)-ethoxy]-quinolin-2-yl}-methanone,
6-[2-(1-methyl-pyrrolidin-2-yl)-ethoxy]-quinoline-2-carboxylic acid [2-(tetrahydro-pyran-4-yl)-ethyl]-amide,
6-[2-(1-methyl-pyrrolidin-2-yl)-ethoxy]-quinoline-2-carboxylic acid (3-fluoro-oxetan-3-ylmethyl)-amide,
(2-methyl-pyrrolidin-1-yl)-{6-[2-(1-methyl-pyrrolidin-2-yl)-ethoxy]-quinolin-2-yl}-methanone,
(S)-1-[6-(1-isopropyl-piperidin-4-yloxy)-quinoline-2-carbonyl]-pyrrolidine-2-carbonitrile,
[6-(1-isopropyl-piperidin-4-yloxy)-quinolin-2-yl]-(4-methyl-piperidin-1-yl)-methanone,
(4-hydroxymethyl-piperidin-1-yl)-[6-(1-isopropyl-piperidin-4-yloxy)-quinolin-2-yl]-methanone,
6-(1-isopropyl-piperidin-4-yloxy)-quinoline-2-carboxylic acid isobutyl-amide and
6-(1-isopropyl-pyrrolidin-3-yloxy)-quinoline-2-carboxylic acid cyclohexyl-methyl-amide,
and pharmaceutically acceptable salts thereof.

18. The compound according to claim 1, selected from the group consisting of
[6-(1-isopropyl-piperidin-4-yloxy)-quinolin-2-yl]-(4-methoxy-piperidin-1-yl)-methanone,
[6-(1-isopropyl-piperidin-4-yloxy)-quinolin-2-yl]-(2-methyl-pyrrolidin-1-yl)-methanone,
[6-(1-isopropyl-piperidin-4-yloxy)-quinolin-2-yl]-(2-trifluoromethyl-pyrrolidin-1-yl)-methanone,
azetidin-1-yl-[6-(1-isopropyl-piperidin-4-yloxy)-quinolin-2-yl]-methanone,
6-(1-isopropyl-piperidin-4-yloxy)-quinoline-2-carboxylic acid (3-fluoro-oxetan-3-ylmethyl)-amide,
6-(1-isopropyl-piperidin-4-yloxy)-quinoline-2-carboxylic acid (1-methoxymethyl-cyclopropylmethyl)-amide,
[6-(1-isopropyl-piperidin-4-yloxy)-quinolin-2-yl]-pyrrolidin-1-yl-methanone,
(R)-1-[6-(1-isopropyl-piperidin-4-yloxy)-quinoline-2-carbonyl]-pyrrolidine-2-carbonitrile,
azetidin-1-yl-[6-(3-piperidin-1-yl-propoxy)-quinolin-2-yl]-methanone,
(R)-1-[6-(3-piperidin-1-yl-propoxy)-quinoline-2-carbonyl]-pyrrolidine-2-carbonitrile and (S)-1-[6-(1-isopropyl-piperidin-4-yloxy)-quinoline-2-carbonyl]-pyrrolidine-2-carbonitrile,
and pharmaceutically acceptable salts thereof.

19. A process for the manufacture of a compound according to claim 1, comprising the steps of:
a) reacting a compound of the formula II

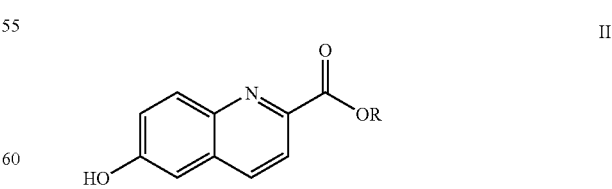

wherein R is lower alkyl,
with an alcohol of the formula III

HO-A  III wherein A is as defined in claim 1, in the presence of a trialkylphosphine or triphenylphosphine and of a diazo compound to obtain a compound of the formula IV

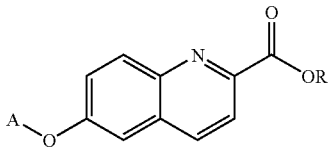

IV and converting the ester of formula IV into the acid of formula V

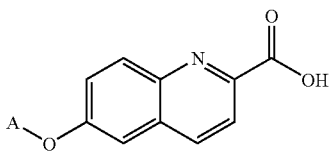

V under acidic or basic conditions, and coupling the compound of formula V with an amine of the formula VI

VI wherein $R^1$ and $R^2$ are as defined in claim 1, with the help of an coupling agent under basic conditions to obtain a compound of the formula I

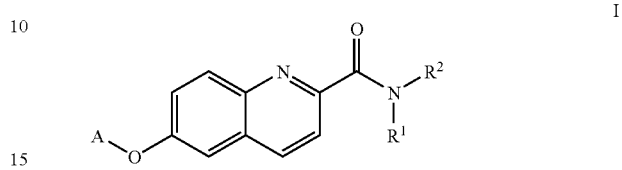

I wherein A, $R^1$ and $R^2$ are as defined in claim 1, and if desired,
converting the compound obtained into a pharmaceutically acceptable salt.

20. A pharmaceutical composition comprising a therapeutically effective amount of a compound according to claim 1 and a pharmaceutically acceptable carrier and/or adjuvant.

* * * * *